(12) United States Patent
Mas Oliva et al.

(10) Patent No.: US 9,539,312 B2
(45) Date of Patent: Jan. 10, 2017

(54) NASAL VACCINE AGAINST THE DEVELOPMENT OF ATHEROSCLEROSIS DISEASE AND FATTY LIVER

(71) Applicant: UNIVERSIDAD NACIONAL AUTÓNOMA DE MÉXICO, Mexico City (MX)

(72) Inventors: Jaime Mas Oliva, Distrito Federal (MX); Blanca Alicia Delgado Coello, Distrito Federal (MX); Victor Guadalupe García Gonzalez, Estado de Mexico (MX); Armando Perez Torres, Distrito Federal (MX)

(73) Assignee: UNIVERSIDAD NACIONAL AUTONOMA DE MEXICO, Mexico City (MX)

( * ) Notice: Subject to any disclaimer, the term of this patent is extended or adjusted under 35 U.S.C. 154(b) by 0 days.

(21) Appl. No.: 14/411,233

(22) PCT Filed: Jun. 26, 2013

(86) PCT No.: PCT/MX2013/000078
§ 371 (c)(1),
(2) Date: Jul. 24, 2015

(87) PCT Pub. No.: WO2014/003531
PCT Pub. Date: Jan. 3, 2014

(65) Prior Publication Data
US 2015/0328296 A1 Nov. 19, 2015

(30) Foreign Application Priority Data

Jun. 28, 2012 (MX) .................... MX/a/2012/007682

(51) Int. Cl.
*A61K 35/74* (2015.01)
*A61K 47/48* (2006.01)
*A61K 39/39* (2006.01)
*A61K 39/00* (2006.01)
*A61K 9/00* (2006.01)
*A61K 9/107* (2006.01)
*A61K 38/08* (2006.01)

(52) U.S. Cl.
CPC ......... *A61K 39/0005* (2013.01); *A61K 9/0043* (2013.01); *A61K 9/1075* (2013.01); *A61K 35/74* (2013.01); *A61K 38/08* (2013.01); *A61K 39/39* (2013.01); *A61K 47/48807* (2013.01); *A61K 2039/543* (2013.01); *A61K 2039/55555* (2013.01); *A61K 2039/622* (2013.01)

(58) Field of Classification Search
CPC ................ A61K 35/74; A61K 2300/00; A61K 2039/543; A61K 2039/55555; A61K 2039/622; A61K 38/08; A61K 39/0005; A61K 39/39; A61K 47/48807; A61K 9/0043; A61K 9/1075
USPC ...... 424/450, 184.1, 185.1, 193.1, 420, 422, 424/812; 436/531, 535, 71, 829, 164, 172, 436/532, 805, 811, 817
See application file for complete search history.

*Primary Examiner* — Padma V Baskar
(74) *Attorney, Agent, or Firm* — Lucas & Mercanti, LLP

(57) ABSTRACT

The present invention provides a novel vaccine compound of micellar nanoparticles to be administered intranasally to treat and/or prevent the disease called atherosclerosis, which results from an abnormal metabolism of circulating lipids. The novelty of the vaccine compound of the present invention is the use of Archaebacterian lipids, lysophosphatidylcholine, and phosphatidylcholine, which give nanoparticles stability and facilitates antigen presentation in its appropriate secondary peptidic conformation. A novel process for the preparation of vaccine compounds which allows obtaining homogeneous nanoparticles with high stability is also presented in this invention.

15 Claims, 9 Drawing Sheets

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Synthetic sequence as appears on US7749721

<400> SEQUENCE: 1

Cys His Leu Leu Val Asp Phe Leu Gln Ser Leu Ser
1               5                   10

<210> SEQ ID NO 2
<211> LENGTH: 31
<212> TYPE: PRT
<213> ORGANISM: Homo sapiens

<400> SEQUENCE: 2

Cys Gln Tyr Ile Lys Ala Asn Ser Lys Phe Ile Gly Ile Thr Glu Phe
1               5                   10                  15

Gly Phe Pro Glu His Leu Leu Val Asp Phe Leu Gln Ser Leu Ser
            20                  25                  30
```

NASAL VACCINE AGAINST THE DEVELOPMENT OF ATHEROSCLEROSIS DISEASE AND FATTY LIVER

CROSS REFERENCE TO RELATED APPLICATION

This application is a 371 of PCT/MX2013/000078 filed on Jun. 26, 2013 which, in turn, claimed the priority of Mexican Patent Application No. MX/A/2012/007682 filed on Jun. 28, 2012, both applications are incorporated herein by reference.

FIELD OF THE INVENTION

The present invention is related to the treatment of atherosclerosis, specifically to the pharmacological compounds addressed at both stopping the development of the atherogenic plaque and also the physiopathologic conditions associated with atherosclerotic disease. More specifically, it is related to a vaccine compound aimed at cholesteryl ester transfer protein (CETP) to prevent and stop the development of atheroslcerosis.

DETAILED DESCRIPTION OF THE INVENTION

Background

According to the World Health Organization (WHO), coronary atherosclerotic disease is the first cause of death worldwide (World Health Organization. Prevention of cardiovascular disease. Guidelines for assessment and management of cardiovascular risk. WHO Press. 2007. ISBN 978 92 4 154717). The impact of this disease on population mortality highlights how important it is to understand its development in order to produce effective preventive clinical measures. WHO calculates that there are about 20 million deaths every year due to this disease, whose treatment represents high costs for national health systems. It is estimated that by the year 2020, about 300 million individuals will die due to acute complications of this disease.

Atherosclerosis is a multifactorial condition. Different risk factors have been described, among which hypertension, hypercholesterolemia, smoking and aging are included (Kullo I. J., Ballantyne C. M. Conditional risk factors for atherosclerosis. *Clin Proc* 2005; 80:219-230). Nevertheless, increasing evidence suggests that the significant damage provoked in the individual by these risk factors is not limited to the atherosclerotic process or its associated complications. Strict clinical trials have proved that the manifestations of atherosclerosis are consequence of the "vulnerable" plaques prone to rupture (Shah P. K. Pathophysiology of plaque rupture and the concept of plaque stabilization. *Cardiol Clin* 2003; 21: 303-314). Such plaques show the highest tendency to make thrombi, the main cause of acute ischemic events in both coronary and brain vessels (Lutgens E., van Suylen R. J., Faber B. C., Gijbels M. J., Eurling P. M., Bijnens A. P., et al. Atherosclerotic plaque rupture: local or systemic process? *Arterioscler Thromb Vasc Biol* 2003; 23: 2123-2130).

Most details about the onset of the atherosclerotic plaque are unknown; yet, some hypotheses have been proposed to explain the events triggering the progression of the disease. One of them postulates oxidative stress as the main cause for the onset of the disease. (Libby P. Inflammation in atherosclerosis. *Nature* 2002; 420:868-874). Atherosclerotic lesions start as fattystreaks, mainly consisting of foam cells surrounded by a layer of endothelial cells with heterogeneous morphology (Jonasson L., Holm J., Skalli O., Bondjers G., Hansson G. K. Regional accumulations of T cells, macrophages, and smooth muscle cells in the human atherosclerotic plaque. *Arteriosclerosis* 1986; 6: 131-138). Streaks are generally developed in areas where the permeability of cell junctions is greater; such condition is thought to facilitate the passage of macromolecules from the tunica intima to the tunica media of the vessel. In early stages of fatty streak formation LDL (Low Density Lipoproteins) are observed gathered in the subendothelial space, even before foam cells appear, thus being the first initiator of this pathology (Iwanaga Y., Tanimura A., Kitsukawa H., Tanigawa J., Aihara M. The role of endothelial cells in the pathogenesis of atherosclerosis. *Acta Pathol Jpn* 1969; 19: 161-178). The plaques become much more complex lesions due to the development of fibrous tissue, calcification, inflammation, ulcer of the arterial wall, and hemorrhages. Occlusion by plaque growth is an important risk factor, although it is the rupture or erosion of the plaque what originates the thrombi leading to heart infarction. (Zarifis J. H. Atherosclerosis, Thrombosis, and inflammatory risk factors, from history and the laboratory to real life. *Eur Heart J* 2005; 26: 317-318).

Results from trials in animals and studies on human atherosclerosis suggest that from all the lesions related to this disease (fatty streaks, fibrous plaques, and complicated lesions) "fatty streak" is the initial lesion of atherosclerosis. These lesions frequently affect the tunica intima of arteries and seem to emerge from focal increases in the contents of lipoprotein in this place; characterized by the deposit and infiltration of lipidic substances, leading to inflammation and the accumulation and proliferation of smooth muscle cells full of lipids (mainly cholesterol oleate), macrophages (foam cells), and fibrous tissue, which narrow the arterial lumen until forming a lesion known as atheroma plaque.

Their formation starts when LDL is trapped in the arterial wall (Karvonen J., Paivansalo M., Kesaniemi Y. A., Horkki S. Immunoglobulin M type of autoantibodies to oxidized low-density lipoprotein has an inverse relation to carotid artery atherosclerosis. *Circulation* 2003; 108: 2107-2112). The accumulation of lipoprotein particles is due not only to an increased permeability of the endothelium, but also the joining of particles to the arterial extracellular matrix (frequently glycosaminoglycans), thus increasing the time they stay within the arterial wall. Once attached to the matrix macromolecules, LDL may suffer oxidative modifications producing hydroperoxides, lysophospholipids, oxysterols, and aldehydic products from the rupture of fatty acids and phospholipids. Based on extensive experimental evidence, it has been proposed that these modifications represent one the key pathological mechanisms in the development of atherogenesis.

Lipoprotein deposits in the arterial wall induce the accumulation of leukocytes, a critical step in lesion formation and, hence, in the pathogenesis of the disease. Therefore, the process known as atherogenesis involves inflammation elements from the start.

The types of inflammatory cells present in the evolving atheroma include monocyte-derived macrophages, as well as lymphocytes. A number of adhesion molecules or leukocyte receptors expressed on the surface of artery endothelial cells participate in the recruitment of leukocytes towards the nascent atheroma (Hansson G. K. Immune mechanisms in atherosclerosis. *Arterioscler Thromb Vasc Biol* 2001; 21: 1876-1890). Likewise, the products of oxidation-modified LDL may raise the expression of leukocyte adhesion molecules. Proinflammatory cytokines may control the expression of adhesion molecules involved in leukocyte recruitment. For instance, interleukin 1 (IL-1) and tumor necrosis factor-alpha (TNF-α) may induce the expression of leukocyte adhesion molecules in endothelial cells. Lipoprotein oxidation products, as well, may induce the release of proinflammatory cytokines in vascular wall cells, providing an additional link between the arterial accumulation of lipoproteins and leukocyte recruitment. Chemoattractant cytokines, as monocyte chemotactic protein-1, seem to direct the migration of leukocytes in the arterial wall.

Once they are on the surface of artery endothelial cells, monocytes and lymphocytes penetrate the endothelial layer, by interacting with adhesion receptors, and dwell in the tunica intima. Here, mononuclear phagocytes mature into macrophages, which become foam cells full of lipids, a transformation that requires modified lipoprotein-receptor mediated endocytosis. Unexpectedly this receptor is not the traditional LDL receptor, since patients and animals lacking effective LDL receptors due to genetic disturbances (e.g.: hypercholesterolemia), have a great number of arterial lesions and extra-arterial xanthomas rich in macrophage-derived foam cells. In addition, exogenous cholesterol suppresses the expression of LDL receptor; therefore, the level of this surface cell receptor for LDL decreases under excessive cholesterol conditions (Brown M. S., Goldstein J. L. A receptor-mediated pathway for cholesterol homeostasis. *Science* 1986; 232: 34-47). Thus, the candidates for alternative receptors able to mediate the entrance of lipids into foam cells include a growing number of macrophage scavenger receptors, which preferably ingest modified lipoprotein, specifically oxidized LDL (ox-LDL).

With the latter process, the adhesion of monocytes to the endothelium, the migration to the intima and the maturing to produce macrophages filled with lipids, represent the key steps in the production of the "fatty streak", precursor of the fully developed atherosclerotic plaque.

One of the mechanisms giving an independent route for the elimination of lipids from the atheroma is the reverse transportation of cholesterol mediated by HDL (high-density lipoprotein). The transfer of cholesterol into the HDL particle involves specialized molecules found on the cell surface, such as ATP-binding cassette transporters (ABC-transporter) (Oram J. F. Tangier disease and ABCA1. *Biochim Biophys Acta* 2000; 1529: 321-330).

In Tangier disease, a condition characterized by the presence of very low levels of HDL, the ABCA1 gene is mutated, so that the flow of cholesterol into nascent HDL particles is altered. The reverse transport of cholesterol mediated by ABCA transporter allows mature cholesterol-loaded HDL deposit it in the hepatocytes, by joining the scavenger receptor classB1.

The transport of lipids from foam cells (macrophages) to peripheral cells such as hepatocytes partially explains the anti-atherogenic action of HDL, as well the described anti-inflammatory and anti-oxidant properties may contribute to the atheroprotective effects of HDL. Therefore, macrophages play an important role in the dynamics of lipid accumulation in the arterial wall during atherogenesis (Linton M. F., Fazio, S. Macrophages, inflammation, and atherosclerosis. *Int J Obes Relat Metab Disord* 2003; 27: S35-S40).

Some lipid-loaded foam cells within the growing intima lesion die because of programmed cell death or apoptosis. Such death of mononuclear phagocytes leads to the formation of a lipid-rich core, commonly called necrotic core, in the stable atherosclerotic plaque. Although the accumulation of lipid-loaded macrophages is a distinctive pattern of the fatty streak, the collection of fibrous tissue formed by the extracellular matrix indicates the most advanced sclerotic lesion; composed of smooth muscle cells and extracellular matrix, rendering a fibroadipose lesion instead of just a mass of macrophage-derived foam cells.

A number of growth factors or cytokines produced by mononuclear phagocytes may stimulate the proliferation of smooth muscle cells and the production of extracellular matrix. Cytokines, like IL-1 (interleukin 1) or TNF-α, found in the plaque, may induce the local synthesis of growth factors, such as platelet-derived growth factor (PDGF), Fibroblast growth factor, among others, contribute to the development of the plaque and its complications. Other cytokines, like Interferon-gamma (IFN-γ) derived from T-cells activated inside the lesion, may limit the production of collagen interstitial forms by smooth muscle cells.

As the disease progresses, atherosclerotic plaques gather calcium. Proteins commonly found in bone may also be present in atherosclerotic lesions (e.g.: osteocalcin, osteopontin, bone morphogenetic proteins) (Jiménez A. E., Damián-Zamacona S., Pérez-Torres A., Moreno A., Mas-Oliva J. Osteopontin Upregulation in Atherogenesis Is Associated with Cellular Oxidative Stress Triggered by the Activation of Scavenger Receptors. *Arch. Med. Res.* 2012; 43: 102-111). Therefore, the plaque mineralization process is similar in many aspects to bone formation.

During the evolution of the atherosclerotic plaque, a complex balance among conditions as the entrance and exit of lipoprotein and leukocytes, proliferation, cell death, production and remodeling of extracellular matrix, as well as neovascularization, contribute to lesion formation (Demer L. L., Watson K. E., Boström K. Mechanism of calcification in atherosclerosis. *Trends Cardiovasc Med* 1994; 4: 45-49). Multiple signals, frequently competitive, control these cellular events, in which a complex combination of mediators is involved.

Lipoproteins, Oxidative Stress and Immune Response

One of the main etiologic factors of atherosclerosis is lipoproteins and their intravascular metabolism, since these particles play an essential role, especially HDL, considered protective, and LDL, considered proatherogenic. Nevertheless, different authors have suggested that the ability of lipoproteins to take part in normal metabolism mainly depends on the amount and characteristics of each one of them. Thus, LDL by itself is not enough to trigger the formation of foam cells, since macrophages do not show a great affinity for native LDL. It has been proposed that the stay of these lipoproteins in the subendothelial space induces chemical modifications on these particles which increase their affinity for macrophages and, therefore, their atherogenic potential (Panasenko O. M., Vol'nova T. V., Azizova O. A., Vladimirov Y. A. Free radical modification of lipoproteins and cholesterol accumulation in cells upon atherosclerosis. *Free Radic Biol Med* 1991; 10: 137-148).

Many modifications have been described under these circumstances, one of the most significant in the stage of fatty streak is oxidation, which may develop by exposure to ROS (reactive oxygen species) generated in different reactions of normal metabolism (Carpenter K. L., Taylor S. E., van deer Veen C, Williamson B. K., Ballantine J. A. Mitchinson M. J. Lipids and oxidised lipids in human atherosclerotic lesions at different stages of development. *Biochim Biophys Acta* 1995; 1256: 141-150). Oxidative stress is paramount not only in the start of lesions, but also in the progression of heart coronary disease.

Diverse studies have postulated that oxLDL accelerates the growth of atherosclerotic lesions by inducing the expression of adhesion molecules, chemokines for monocytes and, for long-term exposure, apoptosis of endothelial cells (Tabas I. Apoptosis and efferocytosis in mouse models of atherosclerosis. *Curr Drug Targets* 2007; 8: 1288-1296). Whereas the presence of fatty streaks does not mean an imminent cardiovascular event, the development of atheromatous plaques depends on them. Hence, it is important to assess the physiologic response of the cells that constitute the luminal and subendothelial vascular surroundings when they are exposed to oxLDL.

Since the development of atherosclerosis is influenced by innate and adaptive immune responses (Hansson G. K., Libby P., Schonbeck U., Yan Z. Q. Innate and adaptive immunity in the pathogenesis of atherosclerosis. *Circ Res* 2002; 91:281-291), a great number of studies have shown the activation of the immune system through different stages during the development of atherosclerosis. Recent trial results suggest that the activation of such immune responses may promote on the one hand atherosclerosis by inducing and perpetuating arterial inflammation; while, on the other hand, the selective activation of certain immune functions may inhibit atherosclerosis and the arterial inflammation. This suggests that new approaches for the treatment and prevention of atherosclerosis are likely, either by selective suppression pro-atherogenic immune responses or the selective activation of antiatherogenic immune responses. Numerous antigens capable of triggering immune response and affecting the development of atherosclerosis have been identified so far. These antigens, along with different adjuvants and different routes of administration, may be useful to modulate immune response.

Trials assessing the effects of immunization on atherosclerosis have focused on two main objectives. First, the presence of pre-existing immune responses considered part of the pathologic process, such as immune response against oxidized LDL epitopes and heat shock protein 60 (HSP 60). Secondly, atherosclerosis-promoting endogenous proteins, like cholesteryl ester transfer protein (CETP) and TNF-$\alpha$. In the first case, the objective is to stimulate immune responses which are protective per se, but which magnitude is no enough, unless they are increased by a vaccine that triggers a more effective immune response or that induce tolerance for undesired immune responses. In the second case, the objective is to produce neutralizing antibodies which inhibit the effect of the chosen antigen.

The identification of key antigens responsible for the activation of immune response related to atherosclerosis is a pre-requirement for the development of immunization therapy. Nevertheless, finding the adjuvant and the most appropriate administration route is also a challenge. Therefore, it is also necessary to understand the mechanisms by which each antigen contributes to the disease to achieve the best combination of antigen and administration vehicle.

As for atherosclerosis, there is plenty of evidence showing that immune activation mainly involves pro-inflammatory Th1 cells, considered responsible for the development of this disease (Binder C. J., Chang M. K., Shaw P. X., Miller Y. I., Hartvigsen K., Dewan A., Witztum J. L. Innate and acquired immunity in atherogenesis. *Nat Med* 2002; 8: 1218-1226). Therefore, adjuvants that favor a change towards antiinflammatory Th2 response, like Alum adjuvant and incomplete Freund's adjuvant, must be more effective tan adjuvants favoring Th1 response. Alternatively, the inhibition of Th1-mediated immune response may be accomplished through tolerance induction by mucosal administration with or without adjuvants like CTB (cholera toxin B subunit) (D'Ambrosio A., Colucci M., Pugliese O., Quintieri F., Boirivant M. Cholera toxin B subunit promotes the induction of regulatory T cells by preventing human dendritic cell maturation. *J. Leukoc Biol* 2008; 84: 661-668).

There is plenty of evidence indicating that the activation of Th1 immune response enhances the aggressiveness of the disease, and counteracts many immunoregulatory points. If this concept is correct, it could be feasible to modulate the disease process by activating or selectively inhibiting specific immune responses. Supporting this possibility, immunization of hypercholesterolemic animals with oxLDL has proved to inhibit atherosclerosis (Stampfer M. J., Sacks F. M., Salvini S., Willett W. C., Hennekens C. H. A prospective study of cholesterol, apolipoproteins, and the risk of myocardial infarction. *N Engl J Med* 1991, 325:373-381). This provides important evidence for atheroprotection through adaptive immune responses in. Thus, these results suggest that during the course of the disease atheroprotective immunity is developed, backing the feasibility of developing a vaccine for the prevention or treatment of atherosclerosis.

Notwithstanding, therapeutic choices for the atherosclerosis have been limited to controlling risk factors (hypercholesterolemia, hypertension, or diabetes mellitus); yet, recent efforts to develop drugs have assessed molecules able to inhibit CETP function. CETP is a proatherogenic hydrophobic glycoprotein which binds HDL in plasma and promotes the transfer of cholesteryl esters and triglycerides among this kind of lipoprotein and low- and very low-density lipoproteins. The most complete trials have been focused on the following drugs:

Anacetrapib (U.S. Pat. No. 7,652,049, CETP inhibitors) ACETP inhibitor developed by Merck to treat hypercholesterolemia and prevent cardiovascular diseases. It is currently in phase III, designed to assess its effects on LDL, HDL and clinically quantifiable cardiovascular events. Phase II studies showed doses correlated with the reduction in HDL-C (HDL-cholesterol) without the corresponding increase in blood pressure in no cohort. The increase in HDL was especially significant, with a average of 44%, 86%, 139%, and 133% in doses of 10 mg, 40 mg, 150 mg, and 300 mg, respectively.

Torcetrapib (Currently Discontinued) (WO 2000/017165)

Developed by Pfizer to treat hypercholesterolemia and prevent cardiovascular diseases. Nevertheless, its development was interrupted in 2006 when phase III trials showed cases of mortality and cardiovascular events in the treatment group receiving a combination of atorvastatin and the drug studied.

Dalcetrapib or JTT-705 (WO 1998/035937)

CETP inhibitor developed by Roche. The phase II trial showed that CETP activity decreased 36%, while HDL cholesterol increased 34% in the group with the highest dose.

Atherosclerosis is a chronic inflammatory disease in which dyslipidemia and inflammation are equally involved in the pathogenesis of the disease. In the last decade, several results from research in vascular biology reveal that endothelial dysfunction and chronic inflammation of the vascular wall are the two most important factors in the development of atherosclerotic lesions. Hence, it is logical to focus the efforts to the development and discovery of new therapies aiming at reestablishing the endothelial function and reducing and controlling inflammation. Advances in this field will render a highly beneficial effect over the control of both disease progression and its acute complications.

Recent discoveries in relation the physiologic bases of the disease have changed radically the traditional concepts about atherosclerosis. It is now clear that atherosclerosis is a chronic inflammatory disease and that the immune system has an important role, both in early stages and in the complications of atherosclerotic plaques. (Riccioni G., De Santis A., Cerasa V., Menna V., Di Ilio C., Schiavone C., et al. Atherosclerotic plaque formation and risk factors. *Int Immunopathol Pharmacol* 2003; 16:25-31). According to alarge number of studies, any current immunomodulatory therapeutic strategy aims at changing one or several of the following important steps in the development of cardiovascular atherosclerotic disease: First, of course, to stop the growth of the atherosclerotic plaque. Second, to have the possibility of accomplishing total or partial regression of the plaque. Third, as a secondary choice, stabilize the plaque. Fourth, stimulate the conditions that diminish the inflammatory process associated with atherosclerotic plaque formation.

Based on the preceding information, some approaches have assessed the possibility of inhibiting atherosclerosis through active immunization or directly administrating blocking antibodies aimed at key proteins in the process of this disease. There is an ongoing first clinical trial using a CETP vaccine (Davidson M. H., Maki K., Umporowicz D., Wheeler A., Rittershaus C., Ryan U. The safety and immunogenicity of a CETP vaccine in healthy adults. *Atherosclerosis* 2003; 169:113-120). On the other hand, some attempts to inhibit the effect of TNF-α through immunization with a recombinant TNF-α molecule have failed to diminish the atherosclerotic process (Hansen P. R., Chew M., Zhou J., Daugherty A., Heegaard N., Jensen P., Mouritsen S., Falk E. Freund's adjuvant alone is antiatherogenic in apoE-deficient mice and specific immunization against TNF alpha confers no additional benefit. *Atherosclerosis* 2001; 158:87-94), while the treatment with antibodies against CD40 ligand has proved to inhibit atherosclerosis in LDLr−/− mice (Mach F., Schonbeck U., Sukhova G. K., Atkinson E., Libby P. Reduction of atherosclerosis in mice by inhibition of CD40 signaling. *Nature* 1998; 394: 200-203). Nevertheless, the first clinical trials using CD40 blockage were stopped due to the side effects.

Atherosclerosis Vaccines

Currently some atherosclerosis vaccines have been developed and have been tried in animals with promising results. Some of them are briefly commented in the following lines:

Vaccine against CD99: (Eva J. A., van Wanrooij, Paula de Vos M., Gabriele Bixel, Dietmar Vestweber, Theo J. C., van Berkel, Johan Kuiper. Vaccination against CD99 inhibits atherogenesis in low-density lipoprotein receptor-deficient mice. *Cardiovasc Res* 2008; 78; 590-596). It has been reported recently that CD99, a leukocyte plasma membrane, originally described in T-cell activation and in lymphocyte aggregation (Allison, A. C. Squalene and squalane emulsions as adjuvants. *Methods* 1999; 19: 87-93. Waclavicek M., Majdic O., Stulnig T., Berger M., Sunder-Plassmann R., Zlabinger G. J. et al. CD99 engagement on human peripheral blood T cells results in TCR/CD3-dependent cellular activation and allows for Th1-restricted cytokine production. *J Immunol* 1998; 161: 4671-4678), takes part in human monocyte transmigration in endothelial cell culture (Schenkel A. R., Mamdouh Z., Chen X., Liebman R. M., Muller W. A. CD99 plays a major role in the migration of monocytes through endothelial junctions. *Nat Immunol* 2002; 3: 143-150). Considering that T-cell and monocyte recruitment contributes to the start and progression of atherosclerotic plaques, blocking their transmigration may favor the appearance of protective mechanisms against atherosclerosis.

That study assessed the role of CD99 in the atherosclerotic process by vaccinating atherosclerosis-prone mice against CD99. The vaccine was made cloning the extracellular domain of CD99 on pcDNA3. *Salmonella typhimurium* modified with pcDNA3-CD99 was orally administered. It induced a CD99-specifi cytotoxic response by CD8+ lymphocytes with the further decrease in the number of CD99+ cells. Thus, the vaccine leads to an T-cell-mediated immune response against cells expressing CD99 (CD4+ cells and macrophages). The result is a significant reduction in the production of atherosclerotic lesions in the aortic valve and in the carotid, compared with control mice.

Vaccine against VEGF: (Celletti F. L., Waugh J. M., Amabile P. G. Brendolan A., Hilfiker P. R., Dake M. D. Vascular endothelial growth factor enhances atherosclerotic plaque progression. *Nat Med* 2001; 7: 425-429) Previous studies have found that mice immunization against receptor 2 (flk-1) of the vascular endothelial growth factor (VEGF) to induce anti-CD99T CD8+ cells, also reduces atherosclerosis. The interference in the interaction of VEGF with its main receptor, VEGFR2, might diminish atherogenesis (Hauer A. D., van Puijvelde G. H., Peterse N., de Vos P., vanWeel V., vanWanrooij E. J. et al. Vaccination against VEGFR2 attenuates initiation and progression of atherosclerosis. *Arterioscler Thromb Vasc Biol* 2007; 27: 2050-2057).

Vaccine against VEGFR2: (Hauer A. D., van Puijvelde G. H., Peterse N., de Vos P., vanWeel V., van Wanrooij E. J. et al. Vaccination against VEGFR2 attenuates initiation and progression of atherosclerosis. *Arterioscler Thromb Vasc Biol* 2007; 27: 2050-2057) VEGFR2, or vascular endothelial growth factor receptor 2, is expressed by activated endothelial cells covering the atherosclerotic plaque. Its proatherogenic effect is based on the fact that the coupling between VEGF and VEGFR2 induces inflammatory responses on endothelial cells by activation of NF-κB, leading to a high expression of adhesion molecules on endothelial cells (for instance, VCAM-1, ICAM-1 and E-selectin), thus increasing monocyte adherence (Kim I., Moon S. O., Kim S. H., Kim H. J., Koh Y. S., Koh G. Y. Vascular endothelial growth factor expression of intercellular adhesion molecule 1 (ICAM-1), vascular cell adhesion molecule 1 (VCAM-1), and E-selectin through nuclear factor-kappa B activation in endothelial cells. *J Biol Chem* 2001; 276: 7614-7620).

*S. typhimurium* with a VEGFR2-codifying plasmid was used in these studies, which developed a cytotoxic CD8+ cell response against cells overexpressing VEGFR2 in atherosclerosis-prone mice. This vaccination attenuated both the start and progression of atherosclerosis, since it decreases the number of activated cells covering the plaque. Nevertheless, VEGFR2 expression increases neo-intimal formation as a side effect, which is an example of the importance of cells overexpressing VEGFR2 in stenotic vascular processes.

Vaccines against an apoB peptide: (Fredrikson G. N., Björkbacka H., Söderberg I., Ljungcrantz I., Nilsson J. Treatment with apo B peptide vaccines inhibits atherosclerosis in human apo B-100 transgenic mice without inducing an increase in peptide-specific antibodies. *J Intern Med* 2008; 264: 563-570). The immunization hypercholesterolemic mice with some apolipoprotein (apo) B-100 peptides, identified as the main responsible for the autoimmune response involved in the atherosclerotic process, significantly reduced the development of atherosclerosis (Fredrikson G. N., Andersson L., Soderberg I., et al. Atheroprotective immunization with MDA-modified apo B-100 peptide sequences is associated with activation of Th2 specific antibody expression. *Autoimmunity* 2005; 38: 171-179). The most effective peptides in these studies corresponded to amino acids 661-680 (p45) and 3136-3155 (p210).

Pilot vaccines having apo B-100 p45 and p210 using Alum as coadjuvant and cBSA as transporter, inhibit the development of atherosclerosis in more than 50% in LDL-receptor knockout mice expressing human apo B-100. They also show an apo B autoantibody pattern similar to the one observed in humans. A mechanism proposed for the functioning of these vaccines is related to regulatory T cell activation. Dendritic cells in charge of presenting antigens to T cells in a non-inflammatory environment or in the absence of a simultaneous activation of Toll-like receptors, normally produces T cell anergy or regulatory T cell activation resulting in a tolerance (Lee H. K., Iwasaki A. Innate control of adaptive immunity: dendritic cells and beyond. *Semin Immunol* 2007; 19: 48-55).

Vaccine against CETP: (Xiying Y., Xiaorong Y., Danning C., Dan M., Jie W., Jingjing L. Intranasal immunization with chitosan/pCETP nanoparticles inhibits atherosclerosis in a rabbit model of atherosclerosis. *Vaccine* 2008; 26: 3727-3734) (Gaofu Q., Jun L., Xiuyun Z., Wentao L., Jie W., Jingjing L. Antibody against cholesteryl ester transfer protein (CETP) elicited by a recombinant chimeric enzyme vaccine attenuated atherosclerosis in a rabbit model. *Life Sci* 2005; 77: 2690-2702). CETP is a 476 amino-acid hydrophobic glycoprotein with an important role in lipid metabolism. When there is an overexpression of this protein or its transfer activity is extremely high may lead to atherosclerosis by diminishing HDL-C and increasing LDL-C (Tall A. R. Plasma cholesteryl ester transfer protein and high-density lipoproteins: new insights from molecular genetic studies. *J Int Med* 1995; 237: 5-12) (Gaofu Q., Dan M., Jie W., Liao Z., Li Z., Roqueb R. S., et al. Long-lasting specific antibodies against CETP induced by subcutaneous and mucosal administration of a 26-amino acid CETP epitope carried by heat shock protein 65 kDa in the absence of adjuvants. *Vaccine* 2004; 22: 3187-3194). Because of this, the inhibition of CETP activity through vaccine-induced antibodies, monoclonal antibodies or antisense oligonucleotides, may increase HDL-C and diminish LDL-C levels in plasma and attenuate the development of atherosclerotic lesions in the aorta of laboratory animals.

The inhibition of CETP activity by a vaccine may be a promising treatment for atherosclerosis, since it has many advantages. For instance, the antibodies induced by administering several doses of a vaccine could continuously inhibit CETP activity for a long time in vivo. Hence, a number of research teams have developed recombinant peptides and proteic vaccines to induce the production of specific antibodies against CETP and reduce aortic lesions (Gaofu Q., Jun L., Xin Y., Wentao L., Jie W., Xiuyun Z., et al. Vaccinating rabbits with a cholesteryl ester transfer protein (CETP) B-cell epitope carried by heat shock protein-65 (HSP65) for inducing anti-CETP antibodies and reducing aortic lesions in vivo. *J Cardiovasc Pharmacol* 2005; 45: 591-598) (Davidson M. H., Maki K., Umporowicz D., Wheeler A., Rittershaus C., Ryan U. The safety and immunogenicity of a CETP vaccine in healthy adults. *Atherosclerosis* 2003; 169: 113-120).

In the first studies accomplished by Gaofu et al. (Gaofu Q., Dan M., Jie W., Liao Z., Li Z., Roqueb R. S., et al. Long-lasting specific antibodies against CETP induced by subcutaneous and mucosal administration of a 26-amino acid CETP epitope carried by heat shock protein 65 kDa in the absence of adjuvants. *Vaccine* 2004; 22: 3187-3194), the Hsp65-CETPC vaccine was produced, made from the fusion of 65 kDa heat shock protein (Hsp65) from *Mycobacterium tuberculosis* var. *Bovis* with the epitope of the linear polypeptide of CETP C terminus (CETPC), and was expressed in *E. coli* as soluble protein. The vaccine was tested in the absence of adjuvants; nevertheless, the results obtained by these researchers showed that the administration of this vaccine to mice, whether subcutaneously or intranasally, triggers immunological responses. In addition, it is possible to obtain a large number of specific anti-CETP antibodies for more than 12 weeks after 3 subcutaneous or 6 intranasal administrations. The latter proves wrong the concept stating that the administration of antigens through mucosal route cannot stimulate a strong immune response. In this study it was shown that by using Hsp65 as co-transporter to present CETPC may stimulate a long-lasting immune response against CETP in mice, even in the absence of co-adjuvants.

One year later, the same team showed that rabbit immunization using the chimeric recombinant enzyme AnsB-TTP-CETPC, which contains asparaginase (AnsB), the epitope of helper T cells which contains residues 831 to 854 of tetanus toxin (TTP), and B cell epitope containing residues 448 to 476 of human CETP (CETPC), in Freund's adjuvant, could overcome the lack of immune response to the auto-antigen CETP. The recombinant vaccine AnsB-TTP-CETPC in Freund's adjuvant, proved the possibility of inducing high levels of anti-CETP antibodies in mice. Nevertheless, since due to its toxicity, Freund's adjuvant is inappropriate to be used in humans, rAnsB-TTP-CETPC with Alum adjuvant (which can be used in humans) was used instead to vaccinate rabbits and stimulate the production of anti-CETP antibodies in vivo. A great antibody titer was obtained in this study, which led to an increase in HDL-C and a decrease in LDL-C, showing an outstanding anti-atherogenic effect in vivo. In addition, the percentage of aortas with "fatty-streak" lesions decreased 42.3%. The results showed that rAnsB-TTP-CETPC vaccine may significantly lower the development of atherosclerosis in rabbits (Gaofu Q., Jun L., Xin Y., Wentao L., Jie W., Xiuyun Z., et al. Vaccinating rabbits with a cholesteryl ester transfer protein (CETP) B-cell epitope carried by heat shock protein-65 (HSP65) for inducing anti-CETP antibodies and reducing aortic lesions in vivo. *J Cardiovasc Pharmacol* 2005; 45: 591-598).

In the same research line, Xiying Yuan et al (Yuan X., Yang X., Cai D., Mao D., Wu J., Zong L., Liu J. Intranasal immunization with chitosan (pCETP) nanoparticles inhibits atherosclerosis in a rabbit model of atherosclerosis. Vaccine 2008; 26: 3727-3734) developed a DNA vaccine against CETP, pCR-X8-HBc-CETP vaccine (abbreviated pCETP), based on the eukaryote expression porter, pCR 3.1-uni, containing eight CpG motifs of 5'-GACGTT-3' as immunostimulant sequence and hepatitis B virus core gen (HBc) inserted with a fragment of DNA encoding 26 residues of human CETP C-terminus (451-476) in the position corresponding to amino acids 80-81 of HBc.

This vaccine administered intramuscularly inhibited the progress of atherosclerosis in rabbits fed on cholesterol, inducing the synthesis of anti-CETP antibodies and altering plasma lipid levels, as well as the protein profile. The same authors proposed a non-invasive medium for the vaccine, intranasal immunization, which is more practical and painless (Kim T. W., Chung H., Kwon I. C., Sung H. C., Kang T. H., Han H. D., et al. Induction of immunity against hepatitis B virus surface antigen by intranasal DNA vaccination using a cationic emulsion as a mucosal gene carrier. *Mol Cells* 2006; 22: 175-181). Considering that most intranasal vaccines induce poor immune responses in the absence of immunostimulants or presentation vehicles, these authors developed an administration system based on quitosan or chitosan, (a chitin-derived polysaccharide) widely studied due to its compatibility, biodegradability, low toxicity and its property to condense DNA, which allows DNA protection from degradation and the improvement of mucosal administration. Those studies proved that intranasal immunization with quitosan/pCETP produces a long-lasting systemic immune response in vivo. Likewise, it may induce the production of anti-CETP antibodies, modulate the lipoproteic profile in plasma and delay the process of atherosclerotic plaque formation in rabbits. Results indicate that intranasal vaccination is equivalent to intramuscular vaccination as for its immunogenicity. Therefore, it has been considered that intranasal vaccination may be a convenient non-invasive route for the administration of DNA vaccines against atherosclerosis. AFFiRiS company is developing a vaccine against atherosclerosis which uses CETP as a protein that causes an effective change in the amount of LDL cholesterol to HDL, using its technology called AFFITOME®. This vaccine is in pre-clinical development (United States Patent Application Publication, US20090104211 A1, Treatment of atherosclerosis).

It is worthy of mention that there is a previous study of CETP vaccine assessed in humans: CETi-1 (Ritterhaus), which consists in the Ceti-1 peptide precipitated in saline solution with a buffer of phosphates and including the aluminum adjuvant, Alhydrogel. Peptide CETi-1 is the acetate salt of the synthetic homodimer disulphate of 31 residues. The sequence is: CQYIKANSKFIGITE/FGFPEHLLVDFLQSLS (SEQ ID NO: 2). The 16 residues of C-terminus (boldface) have the same sequence as residues 461-476 of the C-terminus of human CETP. The 14 residues of the peptide N-terminus (underlined) have the same sequence as residues 830-843 of tetanus toxin. These 14 residues derived from tetanus toxin were used to transform the CETP B cell epitope into an immunogenic molecule. The study had as its aim to show the safety and immunogenicity of a CETP vaccine in healthy adults. Since that was the objective, the authors did not establish a homogenous group in sample size and no strict control was attained. Their studies showed that this vaccine is relatively well tolerated in all the tried doses through a single administration and in a group of patients who received a booster dose. With a single dose only one patient developed anti-CETP antibodies with the highest vaccine dose (250 μg), but with a second dose more than 50% of patients developed an immune response related to the dose. This booster dose proved that repetitive administration of the vaccine is necessary to trigger an adequate antibody response capable of inhibiting CETP activity. It must be emphasize that the booster dose was administered using a suboptimal dose interval; therefore, it was unexpected that the subjects had any reduction in CETP function or in lipid profile. The following challenges emerged:

1. The vaccine with repetitive administrations must induce a sufficient antibody response to auto-antigens (CETP) in a safe manner.
2. Antibody response must be enough to properly inhibit CETP activity and, therefore, increased HDL-cholesterol levels.
3. To show the clinical benefits of increasing HDL cholesterol by inhibiting CETP.

Likewise, other studies have been performed aiming at modulating CETP function. Particularly, Avant Immunotherapeutics, Inc. (Needham, Mass.) has accomplished several attempts, one of them is related to the development of a vaccine based on plasmid DNA encoding for an immunogenic fusion polypeptide which includes the nucleotide sequence of at least one segment encoding for aCETP B cell epitope linked to at least one segment encoding for a broad range helper T cell epitope (U.S. Pat. No. 6,284,553. Plasmid-base vaccine for treating atherosclerosis). The same company has developed a peptide-based vaccine to regulate CETP activity. This vaccine has a peptide which comprises one fragment of a broad range helper T cell epitope joined to the fragment of a CETP B cell epitope, such as its C-terminus (U.S. Pat. No. 6,555,113. Modulation of cholesteryl ester transfer protein (CETP) activity). Another patent registered by Avant Immunotherapeutics consists of a method to increase HDL concentration by stimulating a immune response which inhibits the function of CETP, by immunization with complete CETP or just fragments containing an epitope capable of triggering such immune response (peptides). The peptides may be conjugated with a carrier like KHL (Keyhole Limpet Hemocyanin) or ovalbumin, in order to increase its immunogenicity (U.S. Pat. No. 7,074,407. Methods for increasing HDL cholesterol level). They have also developed a vaccine based on the combination of DNA fragments encoding for one or more CETP B cell epitopes and one or more broad range helper T cell epitope. Plasmids as vaccines administered to laboratory animals provide a response that modulates CETP activity (U.S. Pat. No. 6,846,808. Plasmid-based vaccine for treating atherosclerosis).

Based on this background, different immunomodulatory therapies have started to be developed and some of them are already in clinical trials; for instance, immunosuppressive therapies with cyclosporine and corticosteroids, and therapies using active or passive immunization through vaccination: Active, using peptides derived from proteins associated with normal LDL or oxLDL, HSP or CETP derivative. Some of the formulas already in the phase of clinical trials both in Europe and the United States are: CETP-blocking antibodies in phase II by Avant Immunotherapeutics Inc. (EUA), chimeric antibodies against LDL in phase II by BioInvent Internacional AB (Sweden), and LDL-derivative peptides in phase I within "The atherosclerosis vaccine initiative" carried out by the European-American Consortium for the study of atherosclerosis.

Considering these studies, the present invention proposes new solutions to the problems posed by some technologies involved in the patents or patent applications previously mentioned, with a new intranasal anti-CETP vaccine to inhibit the development of the atherogenic plaque within the arterial lumen using a synthetic peptide as immunogen, consisting of CETP amino acids H486 to S496 (U.S. Pat. No. 7,749,721, Alonso-Garcia, Ana Lucia et al) and a micellar system formed by different types of lipids.

DETAILED DESCRIPTION OF THE INVENTION

Figure 1:
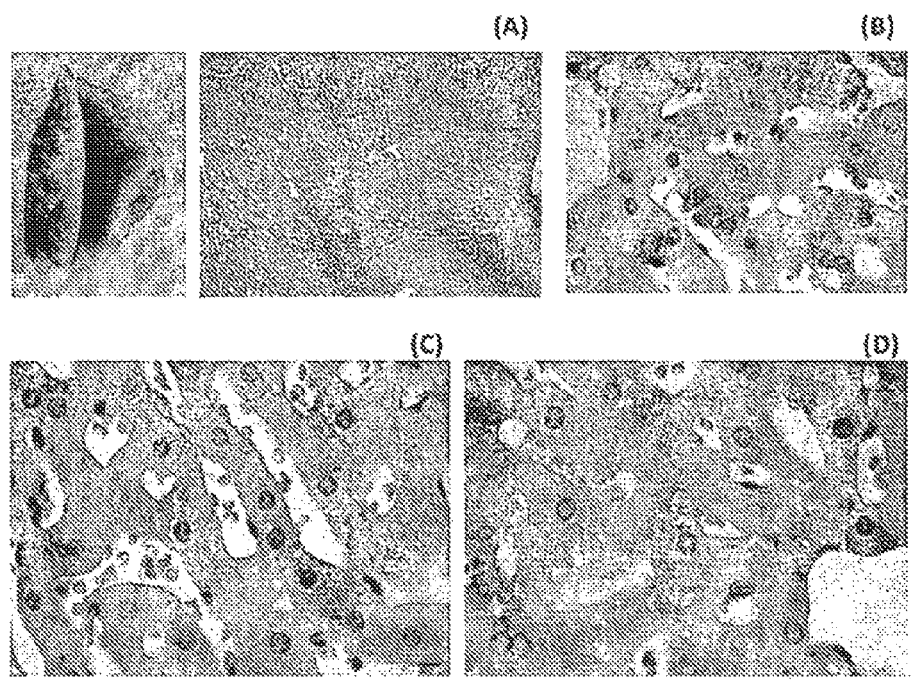
FIG. 1 shows the histological appearance of liver from rabbits fed on normal diet during 30 days. Sinusoid permeability and inside them Kupffer cells were clearly identified. Also, the laminar o mural distribution of normal hepatocytes and their organization in classical lobule, portal lobule, and acinus is well preserved. Portal triads and the associated connective tissue show no abnormalities. Notice the macroscopic aspect and the normal color of the liver of rabbits fed on normal diet at the time of necropsy (upper left angle). Hematoxylin and eosin stain (H&E). Total magnification: A) 100× B) 1000× C) 1000× D) 1000×.

CETP is a hydrophobic glycoprotein joining HDL in blood plasma and promotes the transfer of cholesteryl esters and triglycerides among lipoproteins (Plump A. S., Masucci-Magoulas L., Bruce C., Bisgaier C. L., Breslow J. L., Tall A. R. Increased atherosclerosis in ApoE and LDL receptor gene knock-out mice as a result of human cholesterylester transfer protein trans gene expression. *Arterioscler Thromb Vasc Biol* 1999; 19: 1105-1110), process called lipid heterointerchange. Nevertheless, CETP has also been reported as participating in phospholipid heterointerchange (bidirectional transfer of the same lipid), although the net transfer is mainly carried out by Phospholipid transfer protein (PLTP) (Albers J J, Vuletic S, Cheung M C. Role of plasma phospholipid transfer protein in lipid and lipoprotein metabolism. *Biochim Biophys Acta.* 2012; 1821: 345-357). The movement of cholesteryl esters starts from HDL particles towards triglyceride-rich lipoproteins such as LDL and VLDL; CETP also transfers triglycerides from LDL and VLDL towards HDL, which causes a change in the composition, size, and spherical structure of HDL (Rye K. A., Hime N. J., Barter P. J. The influence of cholesteryl ester transfer protein on the composition, size, and structure of spherical, reconstituted high density lipoproteins. *J Biol Chem* 1995; 270:189-196).

Extensive studies on CETP polymorphims and genetic deficiencies of this protein suggest a direct relation between CETP, HDL-cholesterol levels and cardiovascular disease; nevertheless, many aspects of CETP biological functions have not been discovered yet, neither the molecular bases related to the joining and transfer of lipids (Hall J., Qiu X. Structural and biophysical insight into cholesteryl ester-transfer protein. *Biochem Soc Trans* 2011; 39: 1000-10005).

CETP is constituted of 476 residues, has a molecular weight of 66 kDa, residues $Asp_{88}$, $Asp_{240}$, $Asp_{341}$ y $Asn_{396}$ are glycosylated, it has five free cysteines and a high content of hydrophobic residues compared to other plasmatic proteins (about 44%). The tridimensional structure of CETP with a resolution of 2.2 Å was reported by the beginning of 2007. In general terms, the crystal reflects a long structure boomerang-like shaped, with dimensions of 135×30×35 Å and a folding similar to that of BPI (bactericidal/permeability-increasing protein). The structural description of CETP may be in four domains: a barrel on each side of the protein, called N-barrel and C-barrel, a central connecting β-sheet between both barrels, and a C-terminus extension called X-helix, which is absent in BPI protein; each barrel has β-sheets highly packaged along with two helices (A and B in N-barrel, and A' and B' in C-barrel).

The crystallographic structure reveals a 60 Å-ling tunnel with a volume of 2560 Å. According to this tridimensional structure model, CETP may accommodate two molecules of cholesteryl ester inside and a phospholipid molecule associated to each gate of the tunnel, oriented in such a way that the fatty acid chains are towards the interior of the tunnel and the polar head groups located in interphase with water. The tunnel gates are big enough to let lipids in, one of them is protected by the X-helix in the region of the N-barrel and the through two structures called moving flaps (Ω1 y Ω2) in the region of C-barrel. Likewise, mutagenesis and structural studies suggest that triglyceride and cholesteryl ester molecules (neutral lipids) move along the tunnel passing through the narrow central region with dimensions of 10 Å amplitude and 5 Å high (Qiu X., Mistry A., Ammirati M. J., Chrunyk B. A., Clark R. W., Gong Y., Culp J. S., et al. Crystal structure of cholesteryl ester transfer protein reveals a long tunnel and four bound lipid molecules. *Nat Struct Mol Biol* 2007; 14: 106-113).

Currently, in our laboratory we have found that an alternative or simultaneous possibility to facilitate lipid transport among lipoproteic particles is by forming micellar structures associated to the C-terminus region of CETP (X-helix) when this region is in the structure of α-helix (Garcia-González V.; Mas-Oliva J. Structural Arrangement that Supports Lipid Transfer in the cholesteryl-ester transfer protein (CETP). USA-México Workshop in Biological Chemistry: Multidisciplinary Approaches to Protein Folding, Mexico City, Mexico, 25-27 Mar. 2009).

The resolution of the tridimensional structure of CETP allowed establishing that CETP joins just one lipoprotein at a time through its concave surface. This is a strong basis for the proposal that it operates by a carrying mechanism, in which it accepts neutral lipids from a donating particle, transports them through the aqueous phase and releases them in acceptor lipoproteins (Hamilton J. A., Deckelbaum R. J. Crystal structure of CETP: new hopes for raising HDL to decrease risk of cardiovascular disease? *Nat Struct Mol Biol* 2007; 14: 95-97).

Biochemical studies have proved that CETP shows a high affinity for 10 nm-diameter nascent discoid HDL particles (Kd=20-120 nM), this size coincides with the one observed on the concave curvature of CETP, suggesting that it may join an individual particle of HDL through its concave surface with a modest movement of the X-helix and the moving flap Ω1. In order to adapt to lipoproteins of greater sizes, such as LDL, VLDL, a conformational change in the helices of the N- and C-barrels must take place. Likewise, the protein surface has several polar and hydrophobic residues evenly distributed, which suggest that the interactions with lipoprotein surfaces are equally distributed (Jiang X. C., Bruce C., Cocke T., Wang S., Boguski M., Tall A. R. Point mutagenesis of positively charged amino acids of cholesteryl ester transfer protein: conserved residues within the lipid transfer/lipopolysaccharide binding protein gene family essential for function. *Biochemistry* 1995; 34: 7258-7263) (Desrumaux C., Athias A., Masson D., Gambert P., Lallemant C., Lagrost L. Influence of the electrostatic charge of lipoprotein particles on the activity of the human plasma phospholipid transfer protein. *J Lipid Res* 1998; 39: 131-142).

Therefore, one of the aims of this invention is to create a vaccine that inhibits CETP activity and increases HDL levels using the amino acid sequence H486 to S496 of CETP; that is, the last eleven residues of the protein. This sequence includes three of the four key residues to maintain the lipid joining and transfer capacity; these are $L_{488}$, $F_{491}$ y $L_{495}$. The sequence of the synthetic peptide has homology with no other CETP epitopes or other mammal proteins, it shows a high homology, though, with CETP C-terminus of many species: 100% rabbit, human and monkey; and 90% hamster. Since the peptide is formed by just eleven residues, it presents just one window for recognition by the immunologic system.

The efficiency of the immune response is determined by the administration route. In general, the advantages of a vaccine lie in that they are affordable, highly specific, and, in general, have few adverse effects. Nevertheless, an intramuscularly injected vaccine has the risks of contamination and lesions due to the use of needles; in addition, it requires trained personnel for its administration, thus increasing its cost. That is why in this invention nasal application is proposed, so that not requiring trained personnel for its administration, its cost does not increase. On the other hand, since it is a noninvasive route, the lesions generated by the use of needle, as well as the risk of contamination are avoided. It also more practical and painless, providing a greater acceptance by users, because it may be administered to people of any age in a faster way and without the fear provoked by injections.

Currently some intranasal vaccines approved by FDA (Food and Drug Administration) exist, among them the trivalent vaccine against influenza caused by influenza virus subtypes A and B, commercially known as FluMist®. This vaccine may be administered to people between 2 and 49 years of age and does not require trained personnel (McDonald J., Moore D. FluMistvaccine: Questions and answers—summary. *Paediatr Child Health* 2011; 16: 31). The side effects that normally appear are fever, nasal congestion, and nasal flow.

When manufacturing a nasal vaccine, it must be considered that this route, as a rule, induces poor immunologic responses in the absence of stimulants or delivery vehicles (Hobson P., Barnfield C., Barnes A., Klavinskis L. S. Mucosal immunization with DNA vaccines. *Methods* 2003; 31:217-224). Hence, an appropriate administration system must be developed. Previous studies have described a quitosan-based system (a chitin-derived polysaccharide) widely studied due to its compatibility, biodegradability, and low toxicity. It also has the property to condense DNA, which allows DNA protection from degradation and the improvement of mucosal administration. In this study, plasmid pCR-X8-HBc-CETP (pCETP), encoding for CETP B cell epitope, exhibiting the central particle of hepatitis B virus condensed with quitosan was used to form quitosan/pCETP aggregates. Intranasal immunization with this preparation showed a long-term immune response in vivo, stimulating the production of anti-CETP antibodies, modulates lipoproteic profile in plasma and delays the deformation process of atherosclerotic plaques in rabbits. These results prove that intranasal vaccination is equivalent to intramuscular vaccination as for immunogenicity and suggest that intranasal vaccination may be a noninvasive convenient route for the administration of DNA vaccines.

On the other hand, some CETP inhibitors have been developed and are in clinical trial phase, while others are currently in the preclinical phase (Zhao L., Jin W., Rader D., Packard C., Feuerstein G. A translational medicine perspective of the development of torcetrapib: Does the failure of torcetrapib development cast a shadow on future development of lipid modifying agents, HDL elevation strategies or CETP as a viable molecular target for atherosclerosis? A case study of the use of biomarkers and Translational Medicine in atherosclerosis drug discovery and development. *Biochem Pharmacol* 2009; 78:315-325), although it is likely that such drugs may continue presenting tolerance and adverse reactions. Hence, the use of a vaccine in which booster doses were administered temporarily, might lead to a better tolerance by the patient and, thus, to a reduction in atherosclerosis risks.

One of the novel aspects of the present invention is the use of a vaccine compound constituted by lipids from Archaebacteria cell membranes (54% of total lipids). The use of these preparations has shown that they not only function as humoral adjuvants, but also promote a strong cytotoxic T-cell immune response characterized by long-term memory (Krishnan L., Sad S., Patel G. B., Sprott G. D. Archaeosomes induce long-term CD8+ cytotoxic T cell response to entrapped soluble protein by the exogenous cytosolic pathway, in the absence of CD4+ T cell help. *J Immunol* 2000; 165:5177-5185). In some cases, the immune response is similar to that obtained with the potent, yet toxic, Freund's adjuvant. However, it has been proved that preparations with lipids derived from archaebacteria are not toxic (Patel G. B., Omri A., Deschatelets L., Sprott G. D. Safety of archaeosome adjuvants evaluated in a mouse model. *J Liposome Res* 2002; 12:353-372) (Patel G. B., Ponce A., Zhou H., Chen W. Safety of intranasally administered archaeal lipid mucosal vaccine adjuvant and delivery (AMVAD) vaccine in mice. *Int J Toxicol* 2008; 27:329-339). Actually, a number of successful trials using vaccines based on these lipids have already been performed (Conlan J. W., Krishnan L., Willick G. E., Patel G. B., Sprott G. D. Immunization of mice with lipopeptide antigens encapsulated in novel liposomes prepared from the polar lipids of various Archaeobacteria elicits rapid and prolonged specific protective immunity against infection with the facultative intracellular pathogen, *Listeria monocytogenes. Vaccine* 2001; 19:3509-3517) (Krishnan L., Dennis Sprott G.; Institute for Biological Sciences, National Research Council of Canada. Archaeosomes as self-adjuvanting delivery systems for cancer vaccines. *J Drug Target* 2003; 11:515-522); some even administered through intranasal route using ovalbumin as model antigen in a mice model trial which was successful (Patel G. B., Zhou H., Ponce A., Chen W. Mucosal and systemic immune responses by intranasal immunization using archaeal lipid-adjuvanted vaccines. *Vaccine* 2007; 25:8622-8636).

Archaebacteria represent one of the three primary kingdoms or domains of living organisms. They are unicellular organisms without nuclear envelope and with a low content of deoxyribonucleic acid. They include thermophile, halophile, and acidophile organisms, collectively known as "extremophiles". Some authors have proposed that they are similar to organism living in the primitive biosphere. Many of these species are methanogenic, even those found in freezing environment. Four archaea phylums are known, Euryarchaeota, Crenarchaeota, Korarchaeota y Nanoarchaea. These organisms live in extreme habitats, like hot springs, and highly-saline or highly-alkaline water or in acid conditions. It has made evident that a great number of these organisms may constitute up to 20% of the ocean biomass in "soft" environmental conditions (Peretó J., López-Garcia P., Moreira D. Ancestral lipid biosynthesis and early membrane evolution. *Trends Biochem Sci* 2004; 29: 469-477).

The lipids from the cell membrane of these animals have an important amount of polar lipids which are unique and characteristic, based on the 2, 3-dialkylglycerol skeleton. These alkyl groups are isoprenoid and the simplest molecules derived from this type are derivatives from 2,3-dibiphytanyl-O-sn-glycerol (archeol); for instance, two isoprenoid units of 20 carbons joined at positions sn-2 and sn-3 of glycerol. These alkyl chains are generally saturated; nevertheless, some forms have double bonds in different positions. These molecules have one or two groups of polar head, which may be different with units 2, 3-sn-glycerol joined by C40 alkyl components which are also isoprenoid molecules. For instance, calarcheol (called like this because it is the predominant form in some thermophile archaebacteria), it has two C40 isoprenoid units bonded from positions 2 to 3' and from position 3 to 2' (Chong P. L. G., Archaebacterial bipolar tetraetherlipids: Physico-chemical and membrane properties. *Chem Phys Lipids* 2010; 163:253-265).

Some lipids of this kind have two methyl groups and from one to four cyclopentane rings, whereas Crenarchaeota may have one cyclohexane ring additional to the alkyl chains. Other related molecules with up to eight cyclopentyl rings have been observed in naphthenate deposits during the processing of crude oil. These exist as both phosphor- and glycolipids (or in combination), and as the sulfated form of them. Most groups of the phospholipid polar heads are similar to the ones of organisms of primary kingdoms and include ethanolamine, L-serine, glycerol, myo-inositol, and choline in phosphodiester bond. Nevertheless, it is important to observe that some unique polar groups such as di- and trimethylaminopentanotetrol and eigiycosaminyl-myo-inositol may be found in some Archea species (Koga Y., Morii H. Recent advances in structural research on ether lipids from Archaea Including comparative and physiological aspects. *Biosci Biotechn Biochem* 2005; 69: 2019-2034).

The present invention consists of a vaccine compound for intranasal administration, which uses a preparation of micellar nanoparticles including CETP C-terminus as immunogen, phosphatidylcholine, lysophospholipid and lipids from the cell membrane of Archaebacteria *Thermus aquaticus* as a successful mixture to promote an adaptive immune response in the mammal.

During the development of our vaccine compound a series of conditions were assessed such as lipid concentration and composition. Thus one of the novel aspects of this invention is the use of lysophosphatidylcholine, a molecule that we identified as inducing the formation and stabilization of the α-helix secondary functional structure in the Y-helix peptide (antigen of the vaccine compound). Likewise, a series of phospholipids were assessed in the compound, with different length in the fatty acid chains, modifying the electrostatic properties of the polar head, varying the concentration, even some preparations with cholesterol were assessed. Nevertheless, in all the referred conditions no change in the secondary structure of the antigen were observed, which is the C-terminus peptide of CETP, only lysophosphatidylcholine ($C_{12}$) favored the presentation of the α-helix structure, which is the functional conformation that facilitates the lipid transfer function in CETP. This characterization was accomplished using techniques as spectroscopy with ocular dichroism, fluorescence, and electronic microscopy.

The lipid structure of Archaebacterian lipids composed by long-chain alkyl groups bound by ether bonds with glycerol is a characteristic that allows this molecules to have scaffolding functions in micellar nanoparticles, which, at the same time determines the size and increases in an important manner the stability of such micelles.

After finishing a huge number of trials, the optimal concentration of vaccine components was defined, obtaining the following result, which does not mean being limitative of the present invention, but it means that this is the concentration at which the best results were obtained during the preparation of the unilamelar particles Phosphatidylcholine 3 mM.

Archaebacterian lipids 6 mM.

Lysophosphatidylcholine 2 mM.

Antigen (Y-helix) 2.9 mM.

Therefore, the molar ratio lipid/peptide is 3.8/1, obtaining micellar nanoparticles. Likewise, trials were performed to define and standardize the methodology for manufacturing the vaccine.

Considering the physicochemical properties of the antigen, like hydrophobicity, the isoelectric point and the hydrophobic moment, and with the objective of preventing the appearance of aggregation in the Y-helix peptide, after a series of trials it was determined that pH 9.5 (buffered with a solution of $NaHCO_3/Na_2CO_3$ mM) is an optimal condition that allows solubility and keeps the peptide in monomeric state.

On the other hand, considering the high concentration of the lipid mixture (11 mM), several conditions for the preparation of the micellar nanoparticles were assessed; nevertheless, the method was by using a 10 h drying under continuous $N_2$ flow and an extensive sonication process, which is detailed in the methodology section. So that the molar ratio, 3.8:1 (lipid:peptide), was the best to maintain a high stability of the formula, and preserve the secondary structure in α-helix of Y-helix.

In conclusion, during the development of this invention, a formulation with a great number of advantages was used; while nanoparticles with a homogeneous size and good stability, in which the α-helicoidal functional secondary structure of the antigen is maintained, were produced. This guarantees a directed specific immunological response against the C-terminus of CETP. Particularly, the characteristics of the Archaebacterian lipids permit a system which, unlike other adjuvants, provokes minor side toxic effects, whereas maintains the stability of the formulation and improves the absorption in the mucosa. This technological development may also be the basis for other therapeutic applications.

Preparation of the Vaccine Compound

Materials

L-α-phosphatidylcholine (PC) and 1-Lauril-2-Hydroxi-snglycero 3 phosphocholine (Lyso $C_{12}$) were obtained from Avanti Polar Lipids. The reagents sodium bicarbonate, sodium carbonate, sodium azide, monobasic and dibasic sodium phosphates used in the preparing of the buffer solutions and cholesterol were from Sigma-Aldrich. The preparation of Archaebacterian membrane lipids was made from the organism *Thermus aquaticus* (American Type Culture Collection, ATCC).

Peptide Synthesis

A peptide corresponding to the last 11 residues of the C-terminus end of CETP (CHLLVDFLQSLS, SEQ ID NO: 1) U.S. Pat. No. 7,749,721 (Alonso et al) was synthesized. This peptide has a cysteine residue in its amino end. The so called Y-helix was obtained with purity over 98%. The identity and the degree of purity were compared through HPLC and mass spectrometry.

Dissolution and Quantification of Y-Helix

For the preparation of the vaccine, a Y-helix solution was made at a concentration of 4 mg/ml in $NaHCO_3/Na_2CO_3$ buffer, 50 mM (pH 9.5). The concentration was determined through the absorbance of the peptidic bond at 205 nm, using a UV-Visible HP8452A Spectrophotometer with diodes arranged.

Vaccine Preparation

The lipid mixture designed in this protocol permits keeping the Y-helix antigen in its α-helix functional secondary structure on the surface of the nanoparticles, condition that must promote a greater immunological response once the vaccine is administered. On the other hand, the addition of phosphatidylcholine to the mixture of Archaebacterian lipids and Lysophosphatidylcholine facilitates the manufacturing of the micellar nanoparticles, since it gives them structure and stability. The following procedure has been defined according to several trials performed with the methodologies described in our laboratory.

a) All the material is washed with chloroform and with $H_2O$/Ethanol 1:1 solution.

b) Specific amounts of phosphatidylcholine, Archaebacterian lipids, and $C_{12}$ phospholipid (LisoC$_{12}$) are homogenized in chloroform/methanol 9:1. This mixture is placed under a continuous flow of $N_2$ in the darkness until solvents have evaporated completely (about 10 h).

c) Then, lipids are re-suspended in the carbonate buffer 50 mM (pH 9.5). Immediately after this, it is shaken vigorously for 10 minutes to incorporate the total amount of lipids into the solution.

d) The mixture is then practiced an extensive sonication process to obtain the micellar particles. This step is carried out with Branson equipment (SONIFIER 250 with a 10 mm diameter titanium probe) with pulses of 15 s for 30 s of rest, during 5 intervals of 10 minutes each under $N_2$ flow at 4° C.

e) Once sonication is over, the micellar nanoparticles must settle for 150 minutes at 25° C. in darkness. Then they are centrifuged at 13000 rpm for 15 minutes and are filtrated through membranes with pores of 0.45 µm. Samples of the particles were processed through transmission electron microscopy with the negative staining technique to confirm their correct manufacturing.

f) The peptide is incorporated to the micellar nanoparticles by soft mixing (80 rpm) and incubation at 25° C. for 20 minutes.

g) The preparation is aliquoted and kept refrigerated at 4° C., showing a high stability under this storage conditions.

The final lipid concentrations were as follows: phosphatidylcholine 3 mM, Archaebacterian lipids 6 mM, and Lyso C12 2 mM. The final concentration of the peptide was 4 mg/ml (2.91 mM); the molar ratio of total lipids in relation to the peptide was 3.8/1. Lyso C12 is able to modulate the formulation of the α-helix structure in apolipoprotein segments, as well as in the C-terminus domain of CETP; therefore, it maintains the functional structure of nanoparticles in α-helix of the incorporated peptide.

Examples of Usage

The vaccine compound was tried in White rabbits of the New Zealand species with initial weights of 2.0-2.5 kg, which were kept 12 days on normal diet in the vivarium of the Cellular Physiology Institute, UNAM, as a quarantine period. This facility meets the requirements of the Norma Oficial Mexicana (Official Mexican Regulation) NOM-062-ZOO-1999, entitled Technical Specifications for the Production, Care and Use of Laboratory Animals. In addition to observing this regulation, for animal care and management, also the Guide for the Care and Use of Laboratory Animals backed up by the National Institutes of Health (NIH) of the United States and the Declaration of Helsinki were also observed. 16 rabbits were used.

The normal diet consists of rabbit-specific food 5321 from LabDiet, with the following composition: crude protein not less than 16%; crude fat not less than: 2.5%; crude fiber not more than: 18%; ash not more than: 8%; additional minerals not more than: 2.1%. In the high-cholesterol diet a mixture of cholesterol 1% and corn oil 10% were added to the normal food. All rabbits were fed ad libitum.

After the quarantine period, the administration of the high-cholesterol diet to groups 3, 4 and 5 was started. After 15 days, vehicle and vaccine administration to groups 2, 4 and 5 was started. 50 µl of vehicle and vaccine were nasally administered twice a week. This treatment lasted three months.

The following table summarizes the animal groups used.

TABLE 1

Groups of experimental animals used in the different trials

| Group | Treatment characteristics | Num. of animals |
|---|---|---|
| 1 | Normal diet (control) | 1 |
| 2 | Normal diet + vehicle | 3 |
| 3 | High-cholesterol diet (1%) | 5 |
| 4 | High-cholesterol diet + vaccine | 4 |
| 5 | High-cholesterol diet + vaccine | 3 |

In group 4, high-cholesterol diet started two weeks before vaccine administration.

In group 5, high-cholesterol diet started at the same time of vaccine administration.

After the quarantine period and after 12 hr fast, blood samples were taken from the marginal vein of the ear from the different groups of experimental rabbits, and then every 15 days until the end of treatment. The serum fraction was sent to the Biochemistry Laboratory of the Pathology/Clinical Pathology Department of Facultad de Medicina Veterinaria y Zootecnia, UNAM, for triglyceride and total cholesterol analysis.

After experiments concluded, the animals were sacrificed with a lethal dose of pentobarbital sodium, then cardiac perfusion was performed with Krebs-Ringer solution (Glucose 5 mM, NaCl 1.2 mM, KCl 1.75 mM, NaHCO$_3$ 24 mM, KH$_2$PO$_4$ 1.2 mM, MgSO$_4$ 1.2 mM, EDTA15 mM). Then, representative samples of the liver, thoracic and abdominal aorta, heart, and small intestine were collected.

Histopathologic Analysis of the Liver

Fragments no greater than 1 cm$^3$ were used, which were treated with formaldehyde buffered to neutrality to 10% at 25° C. for 24 hours to continue with the normal histological technique of embedding in paraffin wax and cutting into slices. The samples were oriented to obtain transverse and longitudinal cuts from 4 to 6 µm thick and stained with hematoxylin and eosin (H&E) and with Masson's trichrome stains. The observation of the sections was performed in single blind using an optical microscopy equipped with a digital camera.

The livers of rabbits on normal diet, Group 1, clearly showed the laminar or normal mural organization of hepatocytes, preserving the lobular and acinar organization, as can be seen in FIG. 1A. Adjacent sinusoids were visible all the time, containing numerous circulating erythrocytes as it may be seen in FIGS. 1B, 1C, and 1D. As a rule, no pathologic change was observed in the cytology of any processed sample.

Figure 2:
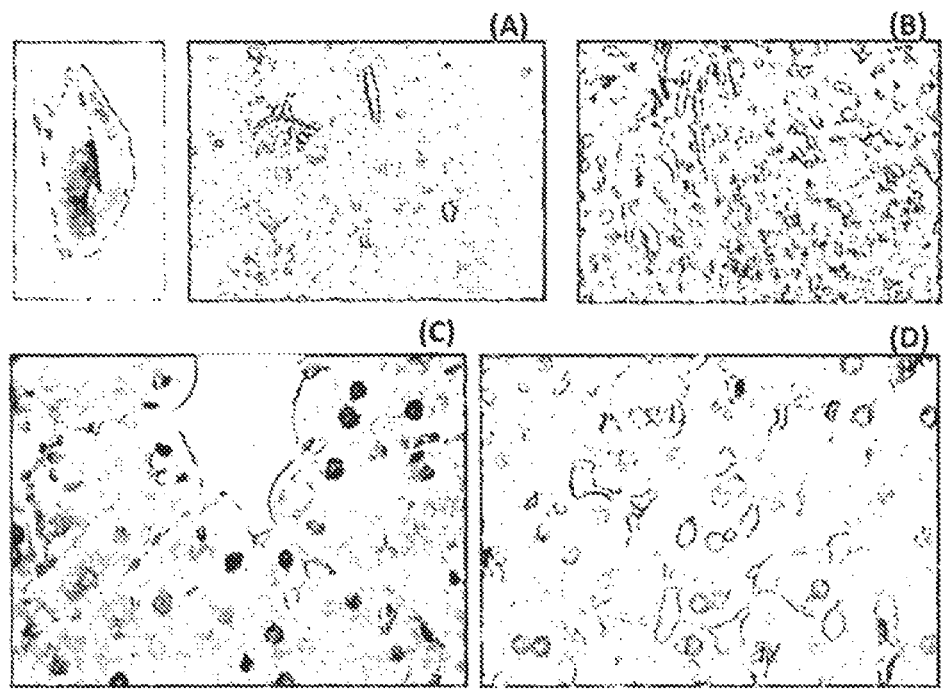
FIG. 2 shows histological sections of liver from rabbits fed on normal diet and administration of placebo for 30 days. In general, the microscopic structure of liver was similar to the one described for rabbits fed on normal diet. Some centrilobular hepatocytes showed minimal steatotic hepatocytes based on the presence of scarce vacuoles. The macroscopic aspect of the liver was also similar to the one of rabbits fed on normal diet. Hematoxylin and eosin stain (H&E). Total magnification: A) 100× B) 400× C) 1000× D) 1000×.

The livers of the animals that received the vehicle and had the normal, Group 2, showed few noticeable changes, as can be seen in FIG. 2. The most common characteristic observed was some steatotic centrilobular hepatocytes with scarce vacuoles. Nevertheless, the sinusoids were visible and preserved the laminar and lobular structure of hepatocytes (FIGS. 2C and 2D).

Figure 3:
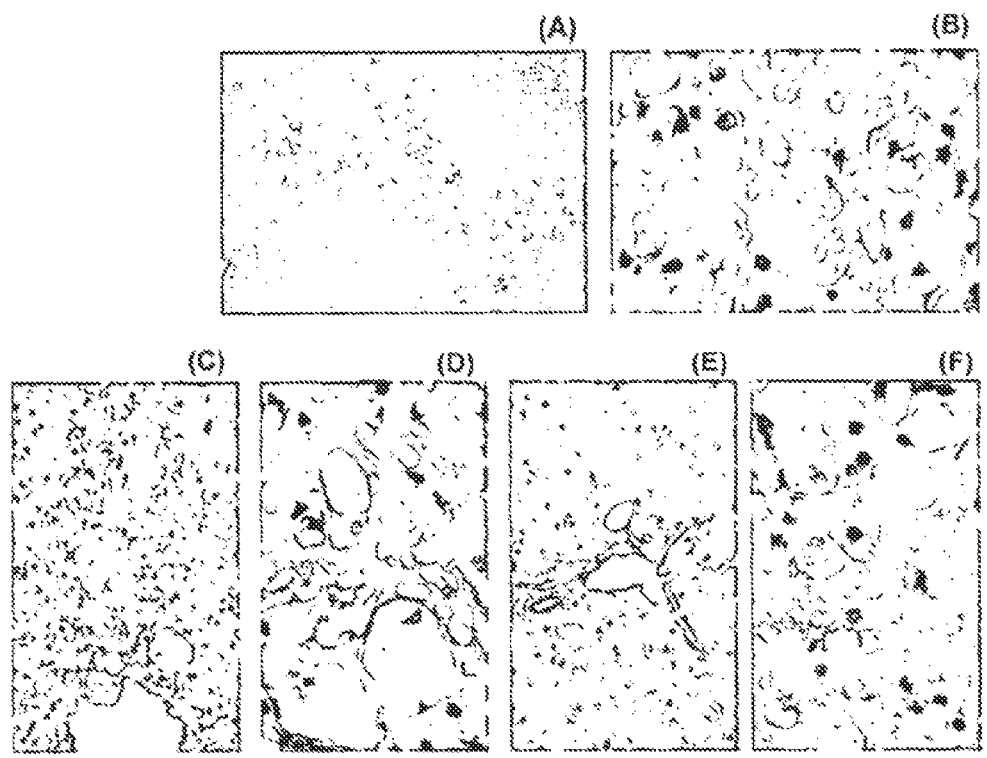
FIG. 3 shows histological sections of liver from rabbits fed on high cholesterol and triglyceride diet for 30 days. The high diet consisted of cholesterol 1% and corn oil 10% added to the balanced food special for rabbits. The main histopathologic changes identified were different degrees of steatosis, both microvacuolar and macrovacuolar, from mild to severe and, in some cases, diffuse, affecting great areas of hepatic parenchyma. In mild to moderate steatosis, centrilobular hepatocytes are mainly affected, which show a microvacuolar cytoplasmic appearance, with no displacement of nuclei to the cellular periphery. In severe steatosis, the sections showed centrilobular hepatocytes and hepatocytes from the paracentral region of the lobule (about 70% of the lobule) with a great overlapping of the two main morphological patterns: microvacuolar and macrovacuolar steatosis in which lipid drops are greater and coalesce until producing a great vacuole whose nucleus and cytoplasm are moved to the peripheral area of the cell. Notice the macroscopic creamy appearance of the liver, clearly different from FIGS. 1 and 2, in which animal were fed on normal diet only and placebo, respectively. Total magnification: A) 100× B) 1000× C) 400× D) 1000× E) 400× F) 1000×. H&E.

In contrast, the livers of rabbits fed on high cholesterol diet which received no vaccine, Group 3, showed variable degrees of steatosis, both microvacuolar and macrovacuolar, from mild to severe and, in some cases diffuse, affecting great portions of the hepatic parenchyma as can be seen in FIG. 3. In animals with mild to moderate steatosis, the component mainly affected was the centrilobular hepatocytes, which had a microvacuolar cytoplasmic appearance, although their nuclei were not displaced to the peripheral region of the cell. Some of these hepatocytes showed cytoplasm distention due to the presence of lipid drops (FIGS. 3B, 3C and 3D), which looked like vacuoles because the cell contents had been eliminated by the solvents used during the process of paraffin wax embedding and cutting (FIGS. 3E and 3F). Most hepatocytes from the lobular periphery, close to the portal triads, had normal appearance although some of them showed microvacuolar cytoplasm. The liver that macroscopically always presented a creamy color, showed centrilobular hepatocytes as well as hepatocytes of the paracentral region of the lobule, as a whole almost 70% of the lobule, with a considerable degree of overlapping between the two main morphologic patterns: microvesicular and macrovesicular, as can be seen in FIGS. 3B and 3C, where lipid drops are greater and coalesce until becoming a great drop or vacuole of fat which moves the nucleus and cytoplasm to the periphery of the cell (FIG. 3D). These hepatocytes are hardly recognizable as such, because they have a morphology similar to small adipocytes. Another characteristic found in these animals was that the bile canaliculi are distended and some bile ducts apparently show cholestasis.

The combination of steatosis, the presence of polymorphonuclear leukocytes, monocytes or both, ballooned hepatocytes and areas of necrosis. A datum important to mention is that necrotized hepatocytes were extraordinarily rare, even in the rabbits with the worst hepatic damage; therefore, steatohepatitis was ruled out in the samples studied.

Figure 4:
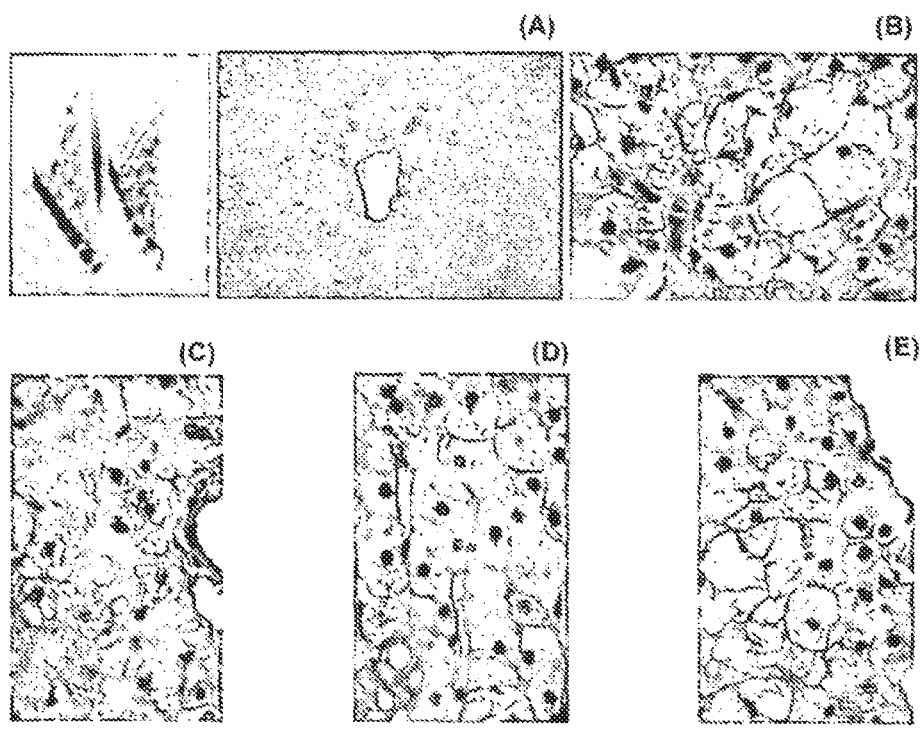
FIG. 4 shows histological sections of liver from rabbits under treatment with a diet high in cholesterol and triglycerides for 15 days, followed by the administration of the intranasal vaccine developed in the present invention. The high diet consisted of cholesterol 1% and corn oil 10% added to the balance food for rabbits. The experiment lasted 30 minutes. The histopathologic changes observed in these animals were similar, although to a lesser degree and extension, to the ones described in the rabbits fed on cholesterol-rich diet without vaccination (FIG. 3). In most cases, only the cells close to the centrilobular veins were affected. Nevertheless, some groups of hepatocytes with macrovacuolar steatosis with a very specific distribution were also observed. Notice that the macroscopic appearance of the livers of rabbits fed on cholesterol-diet and which later received the intranasal vaccine have characteristics intermediate between animal controls and the most affected only fed on cholesterol-rich diet (H&E). Total magnification: A) 100× B) 1000× C) 1000× D) 1000× E) 1000×.

In the rabbits that received a high-cholesterol diet before administering the vaccine, Group 4, showed less changes than the ones described for the rabbits that just received a high-cholesterol diet with no vaccine administration (FIG. 4). In this case, the lesions are more localized and less extended in the lobule (FIGS. 4B, 4C, 4D). In most cases the affectation is restricted to the cells closed to the centrilobular veins (FIG. 4E). However, some groups of hepatocytes with macrovacuolar steatosis of focalized distribution were also observed, as can be seen in the different images of FIG. 4.

Figure 5:
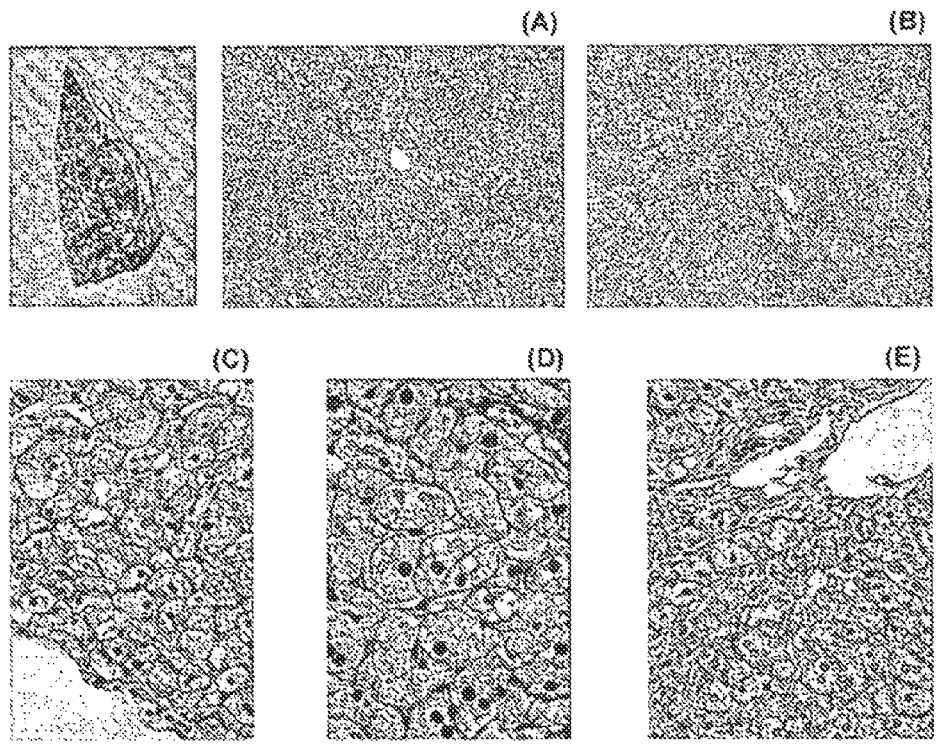
FIG. 5 shows histological sections of liver from rabbits under a diet high in cholesterol and triglycerides with simultaneous administration of the intranasal vaccine of the present invention for 30 days. The high diet consisted of cholesterol 1% and corn oil 10% added to the balanced food special for rabbits. In this group of animals, centrilobular hepatocytes showed mild microvacuolar steatosis, with a minimal increase in cell size not reaching the advanced hepatocyte vacuolization as happened in the case of rabbits only fed on cholesterol-rich diet. Periportal and paracentral hepatocytes had morphology similar to controls (FIG. 1). See macroscopically the appearance and color of liver from rabbits on high-cholesterol diet and simultaneous administration of the vaccine (H&E). Total magnification: A) 100× B) 100× C) 400× D) 1000× E) 400×.

In the samples of livers from rabbits that received the vaccine and a change in the high-cholesterol diet, simultaneously, Group 5, centrilobular hepatocytes with some microvacuole were found (FIGS. 5C, 5D and 5E), with an apparent size increase, although without hepatocyte ballooning, as in the case of rabbit that only received high-cholesterol diet, as can be seen in FIG. 3. Just like in the former groups, Periportal and paracentral hepatocytes of the lobule show a practically normal appearance, while sinusoids adjacent to the centrilobular vein seem to be somewhat occluded (FIGS. 5C, 5E). The administration of the vaccine simultaneously with the start of the high-cholesterol diet has a protective effect on the hepatic parenchyma, as can be concluded from the minimal cytoplasmic alteration of hepatocytes observed.

Figure 6:
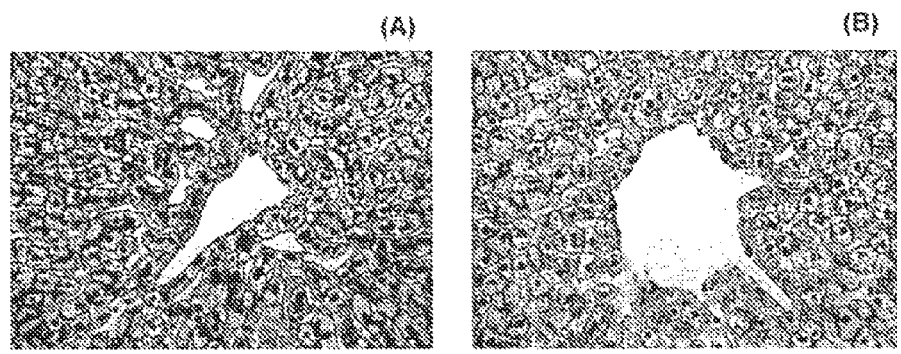
FIG. 6 shows the histological appearance of the liver of rabbits fed on normal diet, without vaccination or vehicle. The histological characteristics are the ones described in FIG. 1. Additionally, collagen fibers are identified, stained blue, near the portal triad (A) and, to a lesser degree, around the central or centrilobular vein (B). Masson's trichrome stain. Total magnification 200×.
Figure 7:
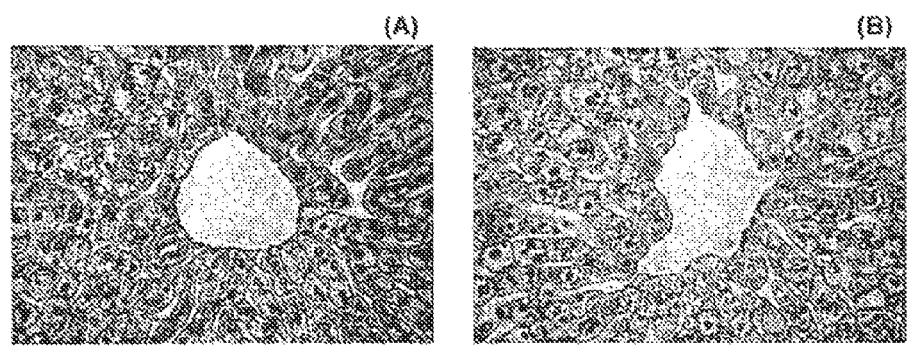
FIG. 7 shows histological sections of liver from rabbits fed on normal diet, without vaccination, but which received vehicle. Notice the histological similarity of the hepatic parenchyma and the distribution of collagen fibers with the group of control rabbits in FIG. 6. Masson's trichrome stain. Total magnification 200×.

FIG. 6 shows the histological sections of the livers of control rabbit fed on normal diet without the administration of vehicle or vaccine, Group 1, stained with Masson's trichrome technique. FIG. 6A shows a normal portal triad in the periphery of the hepatic lobule. FIG. 6B shows the normal structure of a central vein, surrounded by hepatocyte layers, into which sinusoids drain. The histological sections of livers from control animals which received the vehicle intranasally, Group 2, show normal structures as can be seen in FIGS. 7A and 7B, similar to the ones of FIG. 6.

Figure 8:
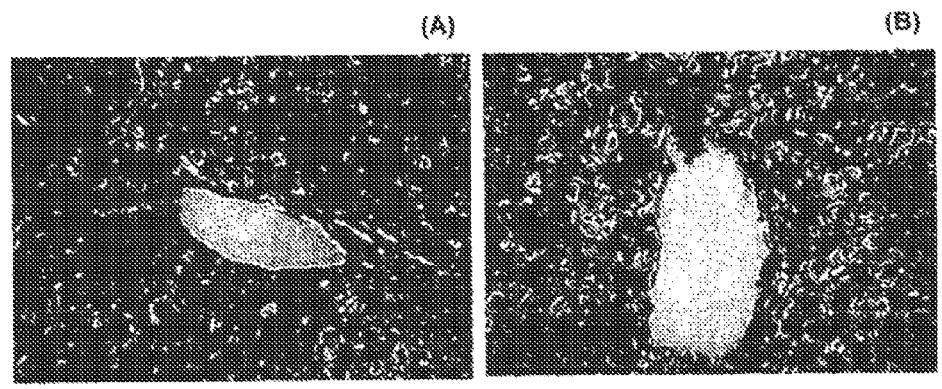
FIG. 8 shows the histological sections of the liver of rabbits fed on high cholesterol and triglyceride diet, without vaccination or vehicle. A) Hepatocytes near the portal triad show a pattern similar to the one of controls (FIGS. 6 and 7); yet, neighboring sinusoids show perisinusoidal fibrosis (blue fibers, arrows). B) Hepatocytes around the central vein show steatosis and some of them are ballooned; additionally, these animals showed perivenular fibrosis (around central veins of hepatic lobules) and a marked perisinusoidal fibrosis. Masson's trichrome stain. Total magnification 200×.
Figure 9:
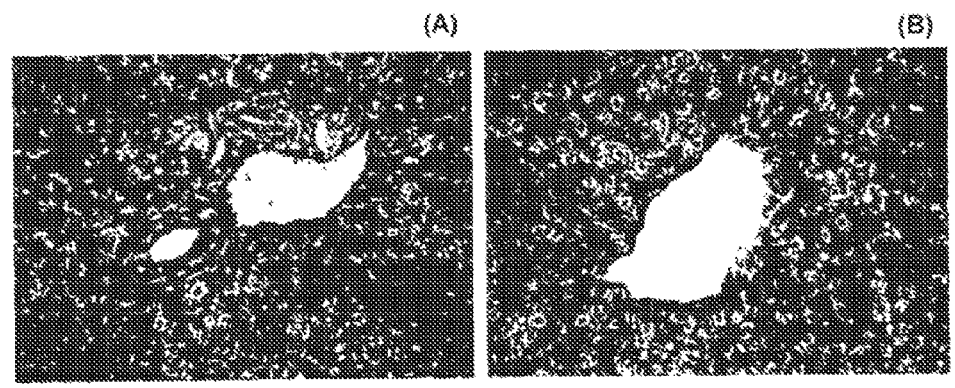
FIG. 9 shows the histological sections of the liver of rabbits treated with high cholesterol and triglyceride diet, which later received the vaccine. A) portal triad, the connective tissue and the surrounding hepatocytes show structural characteristics similar to the ones of controls. B) The central vein and related sinusoids still show fibrosis, although less than that of animals which did not receive the vaccine (FIG. 8). Central hepatocytes were less damaged; some show microvacuolar simple steatosis and ballooned hepatocytes are scarce. Masson's trichrome stain. Total magnification 200×.

In contrast, the histological sections of livers from animals fed on a high-cholesterol and triglyceride diet, without administration of vaccine or vehicle, Group 3, show the development of an important perisinusoidal fibrosis close to the portal triad, as can be seen in FIG. 8A, and of the centrilobular vein (FIG. 8B). These changes are more frequently observed in the zone III of the hepatic acinus, corresponding to the center of the classical lobule. An association between the presence of ballooned hepatocytes and perisinusoidal fibrosis, near the central vein was frequently observed (FIG. 8B).

Figure 10:
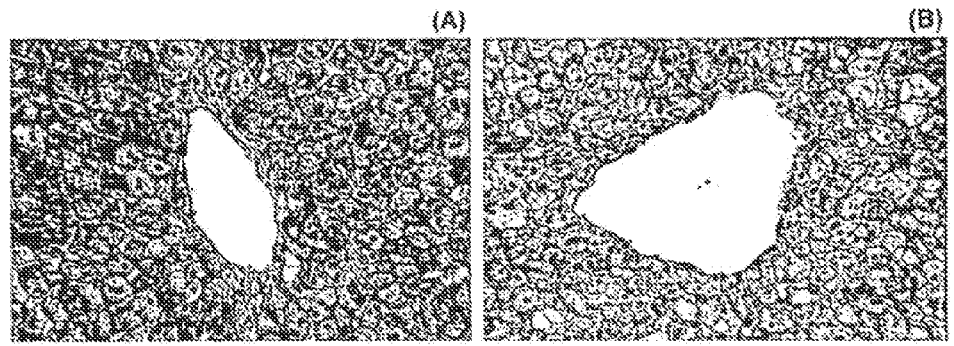
FIG. 10 shows the histological sections of the liver of rabbits fed on high cholesterol and triglyceride diet along with the intranasal vaccine. A) The histological appearance of the portal triad, connective tissue and adjacent parenchyma is practically normal. B) Both centrilobular vein fibrosis and perisinusoidal fibrosis have diminished noticeably compared to what was seen in rabbits fed on high cholesterol and triglyceride diet (FIG. 8). Many centrilobular hepatocytes are still ballooned; few of them have microvesicular steatosis and some show cytoplasm damage. Masson's trichrome stain. Total magnification 200×.

The administration of the vaccine after the starting of high-cholesterol and triglyceride diet, Group 4, significantly improved the histological appearance of the liver as can be seen in FIGS. $9^a$ and 9B; since they showed features similar to the ones of control animals of FIG. 6. The same histological improvement was seen in the liver samples from animals treated with the vaccine at the beginning of the high-lipid diet, Group 5 (FIGS. 10A and 10B).

Histopathologic Analysis of the Abdominal Aorta

Figure 11:
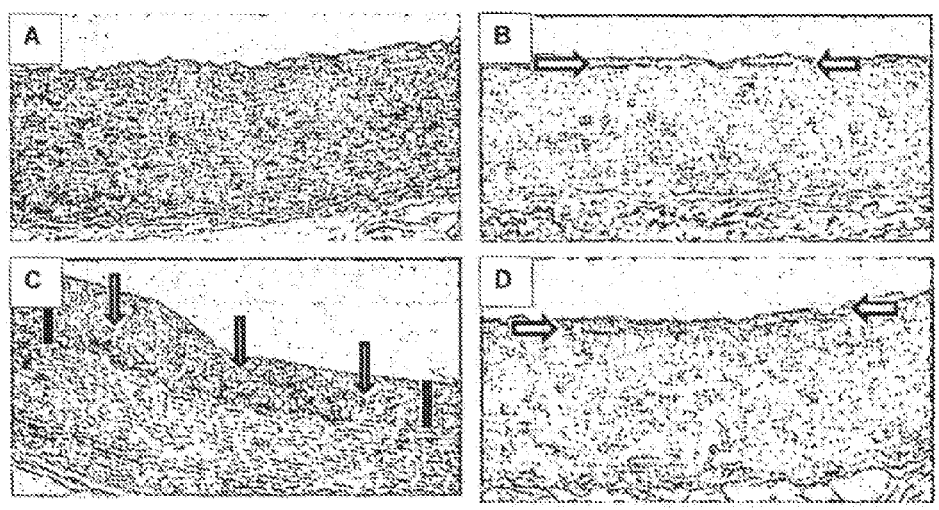
FIG. 11 shows the histological analysis of abdominal aortas, cross-sectioned, of rabbits treated with normal diet (A), with normal diet and vehicle (B), with high cholesterol and triglycerides diet, without intranasal vaccine or vehicle, (C) and rabbits on high cholesterol and triglycerides diet before administration of intranasal vaccine (D). Notice the development of neointima in rabbits that ingested high cholesterol and triglycerides diet with no administration of intranasal vaccine (C, blue arrows and neointima thickness with black bars). Nevertheless, the rabbits on high cholesterol and triglycerides diet that later received the intranasal vaccine developed neointimas significantly thinner (C), similar to the ones of rabbits on normal diet and vehicle (B). Rabbits on normal diet did not show changes in the tunica intima (A). Hematoxylin and eosin stain (H&E). Total magnification: 160×.

The histopathologic analysis showed an evident increase in the thickness of the intima (neointima) of the animals treated just with a high-cholesterol and triglyceride diet, Group 3, as can be seen in FIG. 11C. In animals treated with either placebo (Group 2, FIG. 11B) or high-cholesterol diet before vaccine administration (Group 4, FIG. 11D), no significant thickening of the intima was observed, presenting an appearance closely similar to the observed in the aortas of animals fed on normal diet (FIG. 11A). Based on these observations, we can conclude that treatment with the vaccine formed by micellar nanoparticles is able to delay the process of atherosclerotic plaque formation.

Total Cholesterol and Triglycerides

Figure 12:
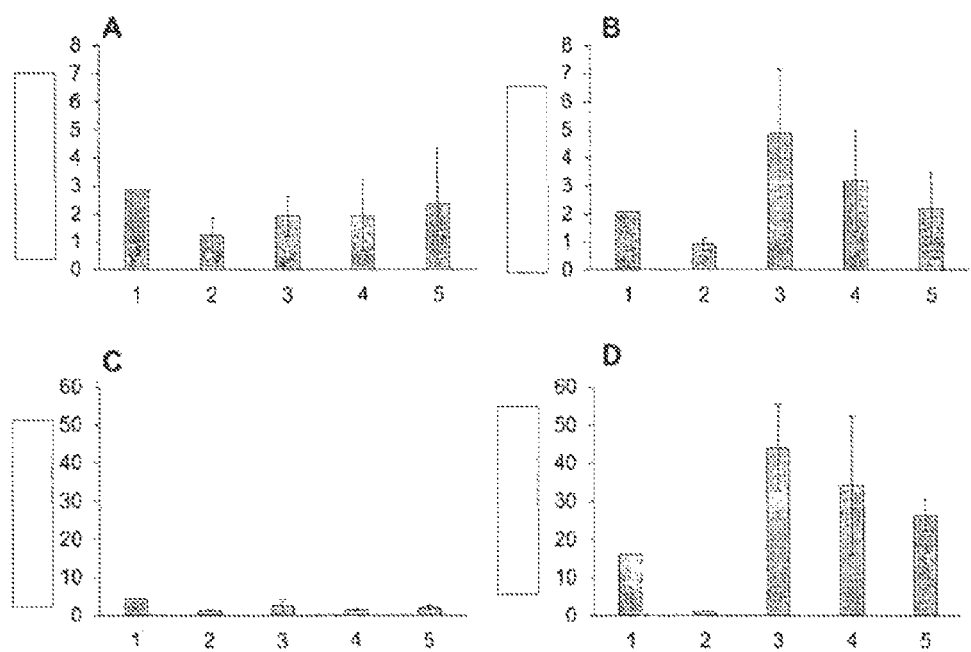
FIG. 12 shows the serum levels of triglycerides and cholesterol in the treatment groups. A) Triglyceride concentrations after quarantine. B) Triglyceride levels after one month treatment. C) Total cholesterol concentrations after quarantine. D) Total cholesterol levels after one month treatment. Group 1 correspond to the control group on normal diet with no vehicle or vaccine; group 2 on normal diet+vehicle; group 3 on high cholesterol and triglyceride diet, group 4 on high cholesterol and triglyceride diet two weeks before starting vaccine administration; and in group 5 high cholesterol and triglyceride diet started at the same time as vaccine administration. LDL levels (mg/dl) group 1, 88.2; average for group 2, 93.7; average for group 3, 121.1; average for group 4, 73.1; average for group 5, 70.0. HDL levels (mg/dl) group 1, 34.1; average for group 2, 36.3; average for group 3, 29.2; average for group 4, 44.6; average for group 5, 49.8.

After one month's treatment (the full treatment lasted three months) a decrease in the serum levels of total cholesterol and triglycerides was observed in the groups that received the vaccine (Groups 4 and 5), being more evident in the Group 5, which started the high-cholesterol diet along with the vaccine administration. The results can be seen in the graphs of FIG. 12.

The results obtained using the formulation described in the present invention prove that intranasal immunization with micellar-nanoparticled vaccine preparation consisting of Archaebacterian lipids, phosphatidylcholine, lysophosphatidylcholine, and carboxyl-terminus of CETP protein, modifies the profile of plasmatic lipoproteins. The level of total cholesterol significantly decreased in the group treated with the vaccine, compared to the group just treated with a high-cholesterol diet. Also HDL-C levels increased in animals fed on high-cholesterol diet and treated with the vaccine compound of the present invention, in relation to the animals with similar diets but not treated with the vaccine compound.

The most important finding using the present invention is that when plasma lipids are higher than normal, and treatment with the vaccine compound of the present invention is administered, a significant decrease in the thickness of the tunica intima of the abdominal aorta is clearly seen, which is directly related to the decrease in the formation of neointima and atherosclerotic plaques. The thickening of the intima and the area of lesions in the aorta were noticeably reduced in the groups treated with the vaccine compound, when compared to the abdominal aortas of animals that did not the vaccine. Another important aspect of the vaccine compound of the present invention is the protection against the development of non-alcoholic fatty liver. This protection is related to a decrease in both microvesicular and macrovesicular steatosis associated with a decrease in perisinusoidal and perivenular fibrosis. All our data suggest that intranasal immunization with lipid/CETP micellar nanoparticles inhibits the progression of the disease known as atherosclerosis.

In conclusion, it is demonstrated that a lipid/CETP micellar-nanoparticled vaccine compound for intranasal administration was developed, which induces anti-CETP antibodies, modulates the profile of plasmatic lipoproteins, delays the process of atheroma-plaque formation in arteries, and protects against the development of non-alcoholic fatty liver. The experimental results presented in this document suggest that nasal vaccination is an appropriate route for the administration of vaccines based on the use of peptides obtained from proteins involved in the development of atherosclerosis such as the Cholesterylester Transfer Protein.

The invention claimed is:

1. A vaccine composition of micellar nanoparticles for intranasal administration comprising a carboxyl terminus peptide of a cholesteryl ester transfer protein (CETP) set forth as SEQ ID NO: 1 as an immunogen, 2,3-dibiphytanyl-o sn-glycerol (calarcheol) from archaebacteria *Thermus aquaticus*, lysophospholipid, and phosphatidylcholine in a pharmaceutically acceptable vehicle.

2. The vaccine composition according to claim 1, wherein the 2,3-dibiphytanyl-o-sn-glycerol (calarcheol) is obtained from cell membranes of archaebacteria *Thermus aquaticus*.

3. The vaccine compound according to claim 1, wherein the 2,3-dibiphytanyl-o-sn-glycerol (calarcheol) is used as scaffolding in micellar nanoparticles providing stability and improving absorption by mucosae.

4. The vaccine composition according to claim 1, wherein the lysophospholipid is lysophosphatidylcholine.

5. The vaccine composition according to claim 4, wherein the lysophosphatidylcholine induces formation and stabilization of an α-helix functional secondary structure on the carboxyl-terminus peptide of CETP, which facilitates the function of lipid transfer on CETP.

6. The vaccine composition according to claim 1, wherein the lysophosphatidylcholine is 1-lauril-2-hydroxi-sn-3-phosphocholine (Lyso $C_{12}$).

7. The vaccine composition according to claim 1, wherein the lipid mixture representing 50% of its components allows the CETP Y-helix antigen to preserve its α-helix functional secondary structure on the surface of the nanoparticles.

8. The vaccine composition according to claim 1, to treat and/or prevent in mammals the development of the disease called atherosclerosis.

9. The vaccine composition according to claim 1, wherein the phosphatidylcholine is L-α-phosphatidylcholine.

10. A vaccine composition of micellar nanoparticles for intranasal administration comprising:
a carboxyl terminus peptide of a cholesteryl ester transfer protein (CETP) set forth as SEQ ID NO: 1 as an immunogen, 2, 3-dibiphytanyl-o-sn-glycerol (calarcheol from archaebacteria *Thermus aquaticus*, 1-lauryl-2-hydroxy-sn-glycero3-phosphocholine (Lyso $C_{12}$) and L α phosphatidylcholine in a pharmaceutically acceptable vehicle.

11. A process for preparing a vaccine composition of micellar nanoparticles to be administered intranasally comprising:
A. synthesizing and purifying an immunogen peptide set forth as SEQ ID NO: 1;
b. isolating cell membranes from *Thermus aquaticus*;
c. isolating 2,3-dibiphytanyl-o-sn glycerol (calarcheol) membrane lipids from the *Thermus aquaticus* cell membranes;
d. incorporating L α phosphatidylcholine, 1-lauryl-2-hydroxy-sn-glycero 3-phosphocholine (Lyso $C_{12}$) and the lipds isolated in step c) to form micelles;
e. incorporating the immunogen peptide from step a) to the micelles prepared in step d).

12. The process according to claim 11, wherein resuspension of lipids performed at pH 9.5 is carried out before step d), which is the optimal to favor the solubility of the peptide and keep it in monomeric state.

13. The process according to claim 11, wherein the immunogenic peptide is incorporated in incubation at 25° C.

14. The process according to claim 11, wherein a lipid:peptide compound is integrated to a vehicle pharmaceutically acceptable for nasal administration.

15. The process according to claim 11, wherein the method produces a micellar-nanoparticled compound of a homogeneous size with high stability, favoring the preservation of the α-helix functional secondary structure of the antigen, which triggers a specific immunologic response specifically aimed at the C-terminus end of CETP.

* * * * *